(12) United States Patent
Boyle

(10) Patent No.: US 6,316,408 B1
(45) Date of Patent: *Nov. 13, 2001

(54) METHODS OF USE FOR OSETOPROTEGERIN BINDING PROTEIN RECEPTORS

(75) Inventor: William J. Boyle, Moorpark, CA (US)

(73) Assignee: Amgen Inc., Thousand Oaks, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,521

(22) Filed: Mar. 30, 1998

Related U.S. Application Data

(63) Continuation-in-part of application No. 08/880,855, filed on Jun. 23, 1997, which is a continuation-in-part of application No. 08/842,842, filed on Apr. 16, 1997, now Pat. No. 5,843,678.

(51) Int. Cl.[7] ................................................. C07K 14/00
(52) U.S. Cl. ............................................. 514/12; 530/350
(58) Field of Search .............................. 514/12; 530/350

(56) References Cited

U.S. PATENT DOCUMENTS 6,017,729   1/2000   Anderson et al. .................. 435/69.1

FOREIGN PATENT DOCUMENTS

WO 98/28424   7/1998   (WO).
WO 99/58674   11/1999   (WO).

*Primary Examiner*—Karen Cochrane Carlson
(74) *Attorney, Agent, or Firm*—Robert B. Winter; Steven M. Odre; Ron K. Levy

(57) ABSTRACT

A novel polypeptide, osteoprotegerin binding protein, involved in osteolcast maturation has been identified based upon its affinity for osteoprotegerin. Nucleic acid sequences encoding the polypeptide, or a fragment, analog or derivative thereof, vectors and host cells for production, methods of preparing osteoprotegerin binding protein, and binding assays are also described. Compositions and methods for the treatment of bone diseases such as osteoporosis, bone loss due to arthritis or metastasis, hypercalcemia, and Paget's disease are also provided.

Receptors for osteoprotegerin binding proteins are also described. The receptors, and agonists and antagonists thereof, may be used to treat bone diseases.

9 Claims, 30 Drawing Sheets

```
GAGCTCGGAT CCACTACTCG ACCCACGCGT CCGGCCAGGA CCTCTGTGAA CCGGTCGGGG    60
CGGGGGCCGC CTGGCCGGGA GTCTGCTCGG CGGTGGGTGG CCGAGGAAGG GAGAGAACGA   120
TCGCGGAGCA GGGCGCCCCGA ACTCCGGGCG CCGCGCC ATG CGC CGG GCC AGC CGA   175
                                         Met Arg Arg Ala Ser Arg
                                          1               5

GAC TAC GGC AAG TAC CTG CGC AGC TCG GAG GAG ATG GGC AGC GGC CCC   223
Asp Tyr Gly Lys Tyr Leu Arg Ser Ser Glu Glu Met Gly Ser Gly Pro
         10                      15                      20

GGC GTC CCA CAC GAG GGT CCG CAG CCC CTG CAC CCC GCG CCT TCT GCA CCG GCT   271
Gly Val Pro His Glu Gly Pro Gln Pro Leu His Pro Ala Pro Ser Ala Pro Ala
             25                      30                      35

CCG GCG CCG CCA CCC CCC GCC GCC TCC ATG TTC CTG GCC CTC CTG   319
Pro Ala Pro Pro Pro Ala Ala Ser Met Phe Leu Ala Leu Leu
         40                      45                      50
```

FIG.1A

```
GGG CTG GGA CTG GGC CAG GTG GTC TGC AGC ATC GCT CTG TTC CTG TAC    367
Gly Leu Gly Leu Gly Gln Val Val Cys Ser Ile Ala Leu Phe Leu Tyr
 55                  60                  65                  70

TTT CGA GCG CAG ATG GAT CCT AAC AGA ATA TCA GAA GAC AGC ACT CAC    415
Phe Arg Ala Gln Met Asp Pro Asn Arg Ile Ser Glu Asp Ser Thr His
                 75                  80                  85

TGC TTT TAT AGA ATC CTG AGA CTC CAT GAA AAC GCA GGT TTG CAG GAC    463
Cys Phe Tyr Arg Ile Leu Arg Leu His Glu Asn Ala Gly Leu Gln Asp
         90                  95                 100

TCG ACT CTG GAG AGT GAA GAC ACA CTA CCT GAC TCC TGC AGG AGG ATG    511
Ser Thr Leu Glu Ser Glu Asp Thr Leu Pro Asp Ser Cys Arg Arg Met
    105                 110                 115

AAA CAA GCC TTT CAG GGG GCC GTG CAG AAG GAA CTG CAA CAC ATT GTG    559
Lys Gln Ala Phe Gln Gly Ala Val Gln Lys Glu Leu Gln His Ile Val
120                 125                 130
```

FIG.1B

```
GGG CCA CAG CGC TTC TCA GGA GCT CCA GCT ATG ATG GAA GGC TCA TGG      607
Gly Pro Gln Arg Phe Ser Gly Ala Pro Ala Met Met Glu Gly Ser Trp
135                 140                 145                 150

TTG GAT GTG GCC CAG CGA GGC AAG CCT GAG GCC CAG CCA TTT GCA CAC      655
Leu Asp Val Ala Gln Arg Gly Lys Pro Glu Ala Gln Pro Phe Ala His
            155                 160                 165

CTC ACC ATC AAT GCT GCC AGC ATC CCA TCG GGT TCC CAT AAA GTC ACT      703
Leu Thr Ile Asn Ala Ala Ser Ile Pro Ser Gly Ser His Lys Val Thr
        170                 175                 180

CTG TCC TCT TGG TAC CAC GAT CGA GGC TGG GCC AAG ATC TCT AAC ATG      751
Leu Ser Ser Trp Tyr His Asp Arg Gly Trp Ala Lys Ile Ser Asn Met
    185                 190                 195
```

FIG.1C

ACG TTA AGC AAC GGA AAA CTA AGG GTT AAC CAA GAT GGC TTC TAT TAC   799
Thr Leu Ser Asn Gly Lys Leu Arg Val Asn Gln Asp Gly Phe Tyr Tyr
200                 205                 210

CTG TAC GCC AAC ATT TGC TTT CGG CAT CAT GAA ACA TCG GGA AGC GTA   847
Leu Tyr Ala Asn Ile Cys Phe Arg His His Glu Thr Ser Gly Ser Val
215                 220                 225                 230

CCT ACA GAC TAT CTT CAG CTG ATG GTG TAT GTC GTT AAA ACC AGC ATC   895
Pro Thr Asp Tyr Leu Gln Leu Met Val Tyr Val Val Lys Thr Ser Ile
235                 240                 245

AAA ATC CCA AGT TCT CAT AAC CTG ATG AAA GGA GGG AGC ACG AAA AAC   943
Lys Ile Pro Ser Ser His Asn Leu Met Lys Gly Gly Ser Thr Lys Asn
250                 255                 260

TGG TCG GGC AAT TCT GAA TTC CAC TTT TAT TCC ATA AAT GTT GGG GGA   991
Trp Ser Gly Asn Ser Glu Phe His Phe Tyr Ser Ile Asn Val Gly Gly
265                 270                 275

FIG.1D

```
TTT TTC AAG CTC CGA GCT GGT GAA GAA ATT AGC ATT CAG GTG TCC AAC    1039
Phe Phe Lys Leu Arg Ala Gly Glu Glu Ile Ser Ile Gln Val Ser Asn
280                 285                 290

CCT TCC CTG CTG GAT CCG GAT CAA GAT GCG ACG TAC TTT GGG GCT TTC    1087
Pro Ser Leu Leu Asp Pro Asp Gln Asp Ala Thr Tyr Phe Gly Ala Phe
295                 300                 305                 310

AAA GTT CAG GAC ATA GAC T GAGACTCATT TCGTGGAACA TTAGCATGGA         1136
Lys Val Gln Asp Ile Asp
            315

TGTCCTAGAT GTTTGGAAAC TTCTTAAAAA ATGGATGATG TCTATACATG TGTAAGACTA  1196

CTAAGAGACA TGGCCCACGG TGTATGAAAC TCACAGCCCT CTCTCTTGAG CCTGTACAGG  1256

TTGTGTATAT GTAAAGTCCA TAGGTGATGT TAGATTCATG GTGATTACAC AACGGTTTTA  1316
```

FIG.1E

```
CAATTTTGTA ATGATTTCCT AGAATTGAAC CAGATTGGGA GAGGTATTCC GATGCTTATG   1376

AAAAACTTAC ACGTGAGCTA TGGAAGGGGG TCACAGTCTC TGGGTCTAAC CCCTGGACAT   1436

GTGCCACTGA GAACCTTGAA ATTAAGAGGA TGCCATGTCA TTGCAAAGAA ATGATAGTGT   1496

GAAGGGTTAA GTTCTTTTGA ATTGTTACAT TGCGCTGGGA CCTGCAAATA AGTTCTTTTT   1556

TTCTAATGAG GAGAGAAAAA TATATGTATT TTTATATAAT GTCTAAAGTT ATATTTCAGG   1616

TGTAATGTTT TCTGTGCAAA GTTTTGTAAA TTATATTTGT GCTATAGTAT TTGATTCAAA   1676

ATATTTAAAA ATGTCTCACT GTTGACATAT TTAATGTTTT AAATGTACAG ATGTATTTAA   1736

CTGGTGCACT TTGTAATTCC CCTGAAGGTA CTCGTAGCTA AGGGGGCAGA ATACTGTTTC   1796

TGGTGACCAC ATGTAGTTTA TTTCTTTATT CTTTTTAACT TAATAGAGTC TTCAGACTTG   1856
```

FIG. 1F

| | | | | |
|---|---|---|---|---|
| TCAAAACTAT | GCAAGCAAAA | TAAATAAAATA | AAAATAAAAT | GAATACCTTG | AATAATAAGT | 1916 |
| AGGATGTTGG | TCACCAGGTG | CCTTTCAAAT | TTAGAAGCTA | ATTGACTTTA | GGAGCTGACA | 1976 |
| TAGCCAAAAA | GGATACATAA | TAGGCTACTG | AAATCTGTCA | GGAGTATTTA | TGCAATTATT | 2036 |
| GAACAGGTGT | CTTTTTTTAC | AAGAGCTACA | AATTGTAAAT | TTTGTTTCTT | TTTTTCCCA | 2096 |
| TAGAAAATGT | ACTATAGTTT | ATCAGCCAAA | AACAATCCA | CTTTTAATT | TAGTGAAAGT | 2156 |
| TATTTTATTA | TACTGTACAA | TAAAAGCATT | GTCTCTGAAT | GTTAATTTTT | TGGTACAAAA | 2216 |
| AATAAATTTG | TACGAAAACC | TGAAAAAAAA | AAAAAAAAAA | AAAAAAAGGG | CGGCCGCTCT | 2276 |
| AGAGGGCCCT | ATTCTATAG | | | | | 2295 |

FIG. 1G

```
         10                         30                          50
AAGCTTGGTACCGAGCTCGGATCCACTACTCGACCTCGCGGCCCCAGGAGCC 70                         90                         110
AAAGCCGGCTCCAAGTCGGCGCGCCCAGTCGAGCCCCGCAGCCTCCGGAGTTGGC 130                        150                         170
CGCAGAGACAAGAGAAGGGGAGGGAGGAGAGCTCCGAAGCGAGAGGGCCGAG 190                        210                         230
CGGCCATGCGCCGCGCCAGCAGAGACTACACCAAGTACCTGCGTGGCTCGGAGGAGATGGG
        M   R   R   A   S   R   D   Y   T   K   Y   L   R   G   S   E   E   M   G 250                        270                         290
CGGCGGCCCCGGCGCCCCGGAGCCCCGACGAGCCCCTGCACGCCCCGCCGCCGCCGCCGCA
  G   G   P   G   A   P   H   E   G   P   L   H   A   P   P   P   P   P   A   P   H 310                        330                         350
CCAGCCCCCCGCCGCCTCCCGCTCCATGTTCGTGGCCCTCCTGGGGCTGGGGCTGGGCCA
  Q   P   P   A   A   S   R   S   M   F   V   A   L   L   G   L   G   L   G   Q 370                        390                         410
GGTTGTCTGCAGCGTCGCCCTGTTCTTCTATTTCAGAGCCAGATGGATCCTAATAGAAT
  V   V   C   S   V   A   L   F   F   Y   F   R   A   Q   M   D   P   N   R   I
```

FIG.4A

```
          430                         470
ATCAGAAGATGGCACTCACTGCATTTATAGAATTTGAGACTCCATGAAAATGCAGATTT
 S  E  D  G  T  H  C  I  Y  R  I  L  R  L  H  E  N  A  D  F 490                         530
TCAAGACACAACTCTGGAGAGTCAAGATACAAAATTAATACCTGATTCATGTAGGAGAAT
 Q  D  T  T  L  E  S  Q  D  T  K  L  I  P  D  S  C  R  R  I 550                         590
TAAACAGGCCTTTCAAGGAGCTGTGCAAAGGAATTACAACATATCGTTGGATCACAGCA
 K  Q  A  F  Q  G  A  V  Q  K  E  L  Q  H  I  V  G  S  Q  H 610                         650
CATCAGAGAGCAGAGAAAGCGATGGTGGATGGCTCATGGTTAGATCTGGCCAAGAGGAGCAA
 I  R  A  E  K  A  M  V  D  G  S  W  L  D  L  A  K  R  S  K 670                         710
GCTTGAAGCTCAGCCTTTTGCTCATCTCACTATTAATGCCACCGACATCCCATCTGGTTC
 L  E  A  Q  P  F  A  H  L  T  I  N  A  T  D  I  P  S  G  S 730                         770
CCATAAAGTGAGTCTGTCCTCTTGGTACCATGATCGGGGTTGGGCCAAGATCTCCAACAT
 H  K  V  S  L  S  S  W  Y  H  D  R  G  W  A  K  I  S  N  M
```

FIG.4B

```
790                         810                         830
GACTTTTAGCAATGGAAAACTAATAGTTAATCAGGATGGCTTTTATTACCTGTATGCCAA
 T  F  S  N  G  K  L  I  V  N  Q  D  G  F  Y  Y  L  Y  A  N 850                         870                         890
CATTTGCTTTCGACATCATGAAACTTCAGGAGACCTAGCTACAGAGTATCTTCAACTAAT
 I  C  F  R  H  H  E  T  S  G  D  L  A  T  E  Y  L  Q  L  M 910                         930                         950
GGTGTACGTCACTAAAAACCAGCATCAAATCCCAAGTTCTCATACCCTGATGAAAGGAGG
 V  V  Y  V  T  K  T  S  I  K  I  P  S  S  H  T  L  M  K  G  G 970                         990                         1010
AAGCACCAAGTATTGGTCAGGGAATTCTGAATTCCATTTTATTCCATAAACGTTGGTGG
 S  T  K  Y  W  S  G  N  S  E  F  H  F  Y  S  I  N  V  G  G 1030                        1050                        1070
ATTTTTTAAGTTACGGTCTCTGGAGAGGAAATCAGCATCGAGGTCTCCAACCCCTCCTTACT
 F  F  K  L  R  S  G  E  E  I  S  I  E  V  S  N  P  S  L  L 1090                        1110                        1130
GGATCCGGATCAGGATGCAACATACTTTGGGGCTTTTAAGTTCGAGATATAGATTGAGC
 D  P  D  Q  D  A  T  Y  F  G  A  F  K  V  R  D  I  D
```

FIG. 4C

```
1150                              1190
CCCAGTTTTTGGAGTGTGTTATGTATTCCTGGATGTTTGGAAACATTTTTAAAACAAGCC 1210                              1250
AAGAAAGATGTATATAGGTGTGTGAGACTACTAAGAGAGGCATGGCCCCAACGGTACACGAC 1270                              1310
TCAGTATCCATGCTCTCTTGACCCTTGTAGAGAACACGCGTATTTACAGCCAGTGGGAGATGT 1330                              1370
TAGACTCATGGTGTGTTACACAATGGTTTTTTAAATTTTGTAATGAATTCCTAGAATTAAA 1390                              1430
CCAGATTGGAGCAATTACGGGTTGACCTTATGAGAAACTGCATGTGGGCTATGGGAGGGG
```

FIG.4D

```
1450                    1470                    1490
TTGGTCCCTGGTCATGTGCCCCTTCGCCAGCTGAAGTGGAGAGGGTGTCATCTAGCGCAAT 1510                    1530                    1550
TGAAGGATCATCTGAAGGGCAAATTCTTTTGAATTGTTACATCATGCTGGAACCTGCAA 1570                    1590                    1610
AAAATACTTTTTCTAATGAGGAGAGAAATATATGTATTTTTATATAATATCTAAAGTTA 1630                    1650                    1670
TATTTCAGATGTAAAGTATTGTTTTCTTTGCAAAGTATTGTAAATTATATTTGTGCTATAGTATT 1690                    1710                    1730
TGATTCAAAATATTTAAAAATGTCTTGCTGTTGACATATTTAATGTTTTAAATGTACAGA 1750                    1770                    1790
CATATTTAACTGGTGCACTTTGTAAATTCCCTGGGGAAAACTTGCAGCTAAGGAGGGGAA 1810                    1830                    1850
AAAAATGTGTTTCCTAATATCAAATGCAGTATATTTCTTCGTTCTTTTTAAGTTAATAG
```

FIG. 4E

```
1870                          1890                         1910
ATTTTTCAGACTTGTCAAGCCTGTGCAAAAAATTAAAATGGATGCCTTGAATAATAAG 1930                          1950                         1970
CAGGATGTTGGCCACCAGGTGCCTTTCAAATTTAGAAACTAATTGACTTTAGAAAGCTGA 1990                          2010                         2030
CATTGCCAAAAGGATACATAATGGGCCACTGAAATCTGTCAAGAGTAGTTATATAATTG 2050                          2070                         2090
TTGAACAGGTGTTTTTCCACAAGTGCCCGCAAATTGTACCTTTTTTTTTTTTCAAATAG 2110                          2130                         2150
AAAAGTTATTAGTGGTTTATCAGCAAAAAGTCCAATTTTAATTTAGTAAATGTTATCTT 2170                          2190                         2210
ATACTGTACAATAAAAACATTGCCTTTGAATGTTAATTTTTTGGTACAAAATAAATTTA 2230                          2250                         2270
TATGAAAAAAAAAAAAAAGGGGCCCTAGAGGCCCTATTCTATAG
```

FIG.4F

FIG. 7A
Toluidine Blue Staining | TRAP staining
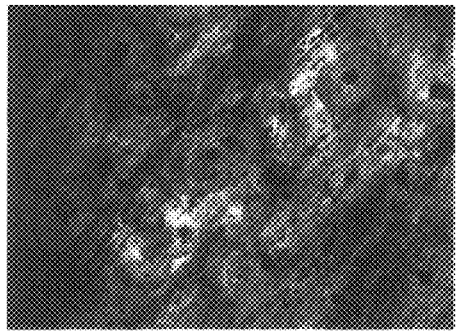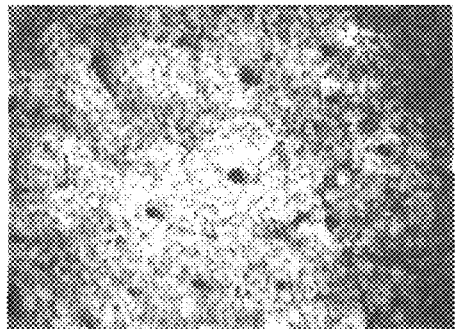
Bone Marrow Cells + M-CSF-1
FIG. 7B
Toluidine Blue Staining | TRAP staining
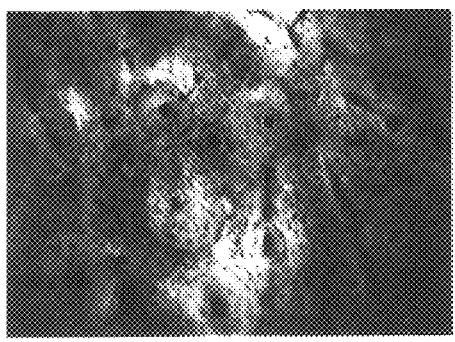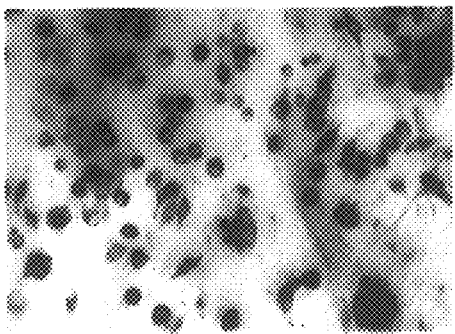
Bone Marrow Cells + OPG Binding Protein
FIG. 7C
Toluidine Blue Staining | TRAP staining
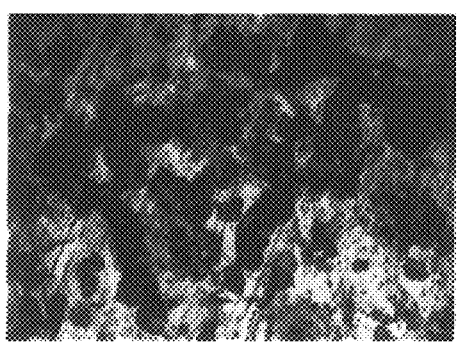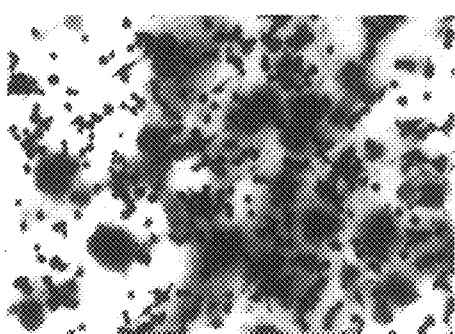
Bone Marrow Cells + M-CSF-1 +OPG Binding Protein

PBS

OPGbp 5ug/d

OPGbp 25ug/d

OPGbp100ug/d

FIG. 10A

```
         10                30                50
ACTCGACCCAGGCGTCCGCCCCGGCCACCGCGCCCATGGACCCGCGGGCCCGGCGGCGCC
                                      M  D  P  R  A  R  R  R  R 70                90               110
GCCAGTGCCCGCGGCTGGCCGCTCTGCGTTCCACTGCAGGTGACTC
 Q  L  P  A  P  L  L  A  L  C  V  L  L  V  P  L  Q  V  T  L 130               150               170
TCCAGGTCACTCCTCCATGCACCCAGGAGAGGCATTATGAGCATCTCGGACGGTGTTGCA
 Q  V  T  P  P  C  T  Q  E  R  H  Y  E  H  L  G  R  C  C  S 190               210               230
GCAGATGCGAACCAGGAAAAGTACCTGTCCTCTAAGTGCACTCCTACCTCCGACAGTGTGT
 R  C  E  P  G  K  Y  L  S  S  K  C  T  P  T  S  D  S  V  C 250               270               290
GTCTGCCCTGTGGCCCCGATGAGTACTTGGACACCTGGAATGAAGAAGATAAATGCTTGC
 L  P  C  G  P  D  E  Y  L  D  T  W  N  E  E  D  K  C  L  L 310               330               350
TGCATAAAGTCTGTGATGCAGGCAAGGCCCTGGTGGCGGTGGATCCTGGCAACCACACGG
 H  K  V  C  D  A  G  K  A  L  V  A  V  D  P  G  N  H  T  A
```

```
                    370                         390                         410
          CCCCGGCGTCGCTGCTTGCACGGGCTGGCTACCACTGGAACTCAGACTGAAGTGCTGCC
           P  R  R  C  A  C  T  A  G  Y  H  W  N  S  D  C  E  C  C  R
                         430                         450                         470
          GCAGGAACACGGAGTGTGCACCTGGCTTCGGAGCTTGCAGCATCCCTTGCAGCTCAACAAGG
           R  N  T  E  C  A  P  G  F  G  A  Q  H  P  L  Q  L  N  K  D
                         490                         510                         530
          ATACGGTGTGCACACCCTGCCTCCTGGGCTTCTTCTCAGATGTCTTTTCGTCCACAGACA
           T  V  C  T  P  C  L  L  G  F  F  S  D  V  F  S  S  T  D  K
                         550                         570                         590
          AATGCAAACCCTTGGACCAACTGCACCCTCCTTGGAAAGCTAGAAGCACACCAGGGGACAA
           C  K  P  W  T  N  C  T  L  L  G  K  L  E  A  H  Q  G  T  T
                         610                         630                         650
          CGGAATCAGATGTGGTCTGCAGCTCTTCCATGACACTGAGGAGACCACCAAGGAGGCCC
           E  S  D  V  V  C  S  S  S  M  T  L  R  R  P  P  K  E  A  Q
```

FIG. 10B

AGGCTTACCTGCCCAGTCTCTCATCGTTCTGCTCCTCTTCATCTCTGTGTAGTAGTGGCTG
A  Y  L  P  S  L  I  V  L  L  F  I  S  V  V  V  A  A

CCATCATCTTCGGCGTTTACTACAGGAAGGGAGGGAAAGCGCTGACAGCTAATTTGTGGA
P  I  I  F  G  V  Y  Y  R  K  G  G  K  A  L  T  A  N  L  W  N

ATTGGGTCAATGATGCTTGCAGTAGTCTAAGTGGAAATAAGGAGTCCTCAGGGACCGTT
W  V  N  D  A  C  S  S  L  S  G  N  K  E  S  S  G  D  R  C

GTGCTGGTTCCCACTCGGCCAACCTCCAGTCAGCAAGAAGTGTGAAGGTATCTTACTAA
A  G  S  H  S  A  T  S  S  Q  Q  E  V  C  E  G  I  L  L  M

TGACTCGGGAGGAGAAGATGGTTCCAGAAGACGGTGCTGGAGCGGTCTGTGGGCCTGTGTG
T  R  E  E  K  M  V  P  E  D  G  A  G  V  C  G  P  V  C  A

CGGCAGGTGGGCCCTGGGCAGAAGTCAGAGATTCTAGGACGTTCACACTGGTCAGCGAGG
A  G  G  P  W  A  E  V  R  D  S  R  T  F  T  L  V  S  E  V

FIG.10C

```
                                        1030                          1050                          1070
TTGAGAGGCAAGGAGAGACCCTCTCGAGGAAGATTCCCACAGAGGATGAGTACACGGACCGGC
 E   T   Q   G   D   L   S   R   K   I   P   T   E   D   E   Y   T   D   R   P
                                        1090                          1110                          1130
CCTCGCAGCCTTCGACTGGTTCACTGCTCCTAATCCAGCAGGAAGCAAATCTATACCCC
 S   Q   P   S   T   G   S   L   L   L   I   Q   Q   G   S   K   S   I   P   P
                                        1150                          1170                          1190
CATTCCAGGAGCCCCTGGAAGTGGGGGGAGAACGACAGTTTAAGCCAGTGTTTCACCGGA
 F   Q   E   P   L   E   V   G   E   N   D   S   L   S   Q   C   F   T   G   T
                                        1210                          1230                          1250
CTGAAAGCACGGGTGGATTCTGAGGGCTGTGACTTCACTGAGCCTCCGAGCAGAACTGACT
 E   S   T   V   D   S   E   G   C   D   F   T   E   P   P   S   R   T   D   S
                                        1270                          1290                          1310
CTATGCCCCGTGTCCCCTGAAAAGCACCTGACAAAGAAATAGAAGGTGACAGTTGCCTCC
 M   P   V   S   P   E   K   H   L   T   K   E   I   E   G   D   S   C   L   P
                                        1330                          1350                          1370
CCTGGGGTGGTCAGCTCCAACTCAACAGAGCTACACAGGCAGTGGSAGTGGGAACACTCCTGGGG
 W   V   V   S   S   N   S   T   D   G   Y   T   G   S   G   N   T   P   G   E
```

FIG.10D

```
1390                    1410                    1430
AGGACCATGAACCCTTTCCAGGGTCCCTGAAATGTGGACCATTGCCCAGTGTGCCTACA
 D  H  E  P  F  P  G  S  L  K  C  G  P  L  P  Q  C  A  Y  S
            1450                    1470                    1490
GCATGGGCTTTCCCAGTGAAGCAGCAGCCAGCATGGCAGAGAGGCGGGAGTACGGCCCCAGG
    M  G  F  P  S  E  A  A  A  S  M  A  E  A  G  V  R  P  Q  D
1510                    1530                    1550
ACAGGGCTGATGAGAGGGGAGAGCCTCAGGGTCCGGGAGCTCCCCAGTGACCAGCCACCTG
 R  A  D  E  R  G  A  S  G  S  G  S  S  P  S  D  Q  P  P  A
            1570                    1590                    1610
CCTCTCTGGGAACGTGACTGGAAACAGTAACTCCACGTTCATCTCTAGCGGCAGGTGATGA
    S  G  N  V  T  G  N  S  N  S  T  F  I  S  S  G  Q  V  M  N
1630                    1650                    1670
ACTTCAAGGGTGACATCATCGTGGTGTATGTCAGCCAGACCTCGCAGGAGGGCCCGGGTT
 F  K  G  D  I  I  V  V  Y  V  S  Q  T  S  Q  E  G  P  G  S
            1690                    1710                    1730
CCGCAGAGCCCGAGTCGGAGCCCGTGGGCCGCCCTGTGCAGGAGGAGACGCTGGCACACA
    A  E  P  E  S  E  P  V  G  R  P  V  Q  E  E  T  L  A  H  R
```

FIG.10E

```
                                       1790
GAGACTCCCTTTGCGGGGCACCCGGCGCCGCGCTTCCCCGAGTTCCCGGACGTCTGTGCCACCGGGGCTGGGC
 D   S   F   A   G   T   A   P   R   F   P   D   V   C   A   T   G   A   G   L
   1750                    1770                    1810                1830                    1850
TGCAGGAGCAGGGGGCAGGGGCACCCCCGGCAGACCCGGCAGAAGGACATCGCGGCCGGTGCAGGAGCAGG
 Q   E   Q   G   A   P   R   Q   K   D   G   T   S   R   P   V   Q   E   Q   G
   1810                    1830                    1850                    1870                    1890                    1910
GTGGGGGCGCAGACTTCACTCCATACCCAGGGGTCCGGACAATGTGCAGAATGACCTCACC
 G   A   Q   T   S   L   H   T   Q   G   S   G   Q   C   A   E
   1930                    1950                    1970
TTCTCTGTCTGCCCTGGGTGCAGGGCACCAGTGCCTTTCCAAAACATGGTGTAGCTAGC
   1990                    2010                    2030
CACTGTGCACCTCCCACTGTGCCCAGGTGCTGCAGGTGCATGGTGATGGAGCCCACCTCTCACT
   2050                    2070
TCCTCCAGTGCCCCCTCCCTCTGCCTCCTAC
```

FIG.10F

\* Different to vehicle treated control p < 0.05.

METHODS OF USE FOR OSETOPROTEGERIN BINDING PROTEIN RECEPTORS

This application is a continuation in part of No. 08/880,855, Jun. 23, 1997, which is a continuation in part of No. 08/842,842 Apr. 16, 1997, U.S. Pat. No. 5,843,678.

FIELD OF THE INVENTION

The present invention relates to polypeptides which are involved in osteoclast differentiation. More particularly, the invention relates to osteoprotegerin binding proteins, nucleic acids encoding the proteins, expression vectors and host cells for production of the proteins, and binding assays. Compositions and methods for the treatment of bone diseases, such as osteoporosis, bone loss from arthritis, Paget's disease, and hypercalcemia, are also described.

The invention also relates to receptors for osteoprotegerin binding proteins and methods and compositions for the treatment of bone diseases using the receptors.

BACKGROUND OF THE INVENTION

Living bone tissue exhibits a dynamic equilibrium between deposition and resorption of bone. These processes are mediated primarily by two cell types: osteoblasts, which secrete molecules that comprise the organic matrix of bone; and osteoclasts, which promote dissolution of the bone matrix and solubilization of bone salts. In young individuals with growing bone, the rate of bone deposition exceeds the rate of bone resorption, while in older individuals the rate of resorption can exceed deposition. In the latter situation, the increased breakdown of bone leads to reduced bone mass and strength, increased risk of fractures, and slow or incomplete repair of broken bones.

Osteoclasts are large phagocytic multinucleated cells which are formed from hematopoietic precursor cells in the bone marrow. Although the growth and formation of mature functional osteoclasts is not well understood, it is thought that osteoclasts mature along the monocyte/macrophage cell lineage in response to exposure to various growth-promoting factors. Early development of bone marrow precursor cells to preosteoclasts are believed to mediated by soluble factors such as tumor necrosis factor-α (TNF-α), tumor necrosis factor-β (TNF-β), interleukin-1 (IL-1), interleukin-4 (IL-4), interleukin-6 (IL-6), and leukemia inhibitory factor (LIF). In culture, preosteoclasts are formed in the presence of added macrophage colony stimualting factor (M-CSF). These factors act primarily in early steps of osteoclast development. The involvement of polypeptide factors in terminal stages of osteoclast formation has not been extensively reported. It has been reported, however, that parathyroid hormone stimulates the formation and activity of osteoclasts and that calcitonin has the opposite effect, although to a lesser extent.

Recently, a new polypeptide factor, termed osteoprotegerin (OPG), has been described which negatively regulated formation of osteoclasts in vitro and in vivo (see co-owned and co-pending U.S. Ser. Nos. 08/577,788 filed Dec. 22, 1995, 08/706,945 filed Sep. 3, 1996, and 08/771,777, filed Dec. 20, 1996, hereby incorporated by reference; and PCT Application No. WO96/26271). OPG dramatically increased the bone density in transgenic mice expressing the OPG polypeptide and reduced the extent of bone loss when administered to ovariectomized rats. An analysis of OPG activity in in vitro osteoclast formation revealed that OPG does not interfere with the growth and differentiation of monocyte/macrophage precursors, but more likely blocks the differentiation of osteoclasts from monocyte/macrophage precursors. Thus OPG appears to have specificity in regulating the extent of osteoclast formation.

OPG comprises two polypeptide domains having different structural and functional properties. The amino-terminal domain spanning about residues 22–194 of the full-length polypeptide (the N-terminal methionine is designated residue 1) shows homology to other members of the tumor necrosis factor receptor (TNFR) family, especially TNFR-2, through conservation of cysteine rich domains characteristic of TNFR family members. The carboxy terminal domain spanning residues 194–401 has no significant homology to any known sequences. Unlike a number of other TNFR family members, OPG appears to be exclusively a secreted protein and does not appear to be synthesized as a membrane associated form.

Based upon its activity as a negative regulator of osteoclast formation, it is postulated that OPG may bind to a polypeptide factor involved in osteoclast differentiation and thereby block one or more terminal steps leading to formation of a mature osteoclast.

It is therefore an object of the invention to identify polypeptides which interact with OPG. Said polypeptides may play a role in osteoclast maturation and may be useful in the treatment of bone diseases.

SUMMARY OF THE INVENTION

A novel member of the tumor necrosis factor family has been identified from a murine cDNA library expressed in COS cells screened using a recombinant OPG-Fc fusion protein as an affinity probe. The new polypeptide is a transmembrane OPG binding protein which is predicted to be 316 amino acids in length, and has an amino terminal cytoplasmic domain, a transmembrane doman, and a carboxy terminal extracellular domain. OPG binding proteins of the invention may be membrane-associated or may be in soluble form.

The invention provides for nucleic acids encoding an OPG binding protein, vectors and host cells expressing the polypeptide, and method for producing recombinant OPG binding protein. Antibodies or fragments thereof which specifically bind OPG binding protein are also provided.

OPG binding proteins may be used in assays to quantitate OPG levels in biological samples, identify cells and tissues that display OPG binding protein, and identify new OPG and OPG binding protein family members. Methods of identifying compounds which interact with OPG binding protein are also provided. Such compounds include nucleic acids, peptides, proteins, carbohydrates, lipids or small molecular weight organic molecules and may act either as agonists or antagonists of OPG binding protein activity.

OPG binding proteins are involved in osteoclast differentiation and the level of osteoclast activity in turn modulates bone resorption. OPG binding protein agonists and antagonists modulate osteoclast formation and bone resorption and may be used to treat bone diseases characterized by changes in bone resorption, such as osteoporosis, hypercalcemia, bone loss due to arthritis metastasis, immobilization or periodontal disease, Paget's disease, osteopetrosis, prosthetic loosening and the like. Pharmaceutical compositions comprising OPG binding proteins and OPG binding protein agonists and antagonists are also encompassed by the invention.

Receptors for OPG binding proteins have also been identified from a marine cDNA library constructed from bone marrow cells which bind to a fluorescent-label OPG binding protein. The receptors may be used to identify agonists and antagonists of OPG binding protein interactions with its receptor which may be used to treat bone disease.

DESCRIPTION OF THE FIGURES

FIG. 1. (SEQ ID NOS: 1 and 2) Structure and sequence of the 32D-F3 insert encoding OPG binding protein. Predicted transmembrane domain and sites for asparagine-linked carbohydrate chains are underlined.

FIG. 4. (SEQ ID NOS: 3 and 3) Structure and sequence of the pcDNA/ hu OPGbp 1.1 insert encoding the human OPG binding protein. The predicted transmembrane domain and site for asparagine-linked charbohydrate chains are underlined.

FIG. 7. Osteoclasts derived from bone marrow cells in the presence of both M-CSF and OPG binding protein [158–316] resorb bone in vitro. Bone marrow cells treated with either M-CSF, OPG binding protein, or with both factors combined, were plated onto bone slices in culture wells, and were allowed to develop into mature osteoclasts. The resulting cultures were then stained with Toluidine Blue (left column), or histochemically to detect TRAP enzyme activity (right column). In cultures receiving both factors, mature osteoclasts were formed that were capable of eroding bone as judged by the presence of blue stained pits on the bone surface. This correlated with the presence of multiple large, multinucleated, TRAP positive cells.

FIG. 10. (SEQ ID NOS: 42 and 43) Murine ODAR cDNA sequence and protein sequence. Nucleic acid sequence of the ~2.1 kb cDNA clone is shown, and translation of the 625 residue long open reading frame indicated above. The hydrophobic signal peptide is underlined, and the hydrophobic transmembrane sequence (residues 214–234) is in bold. Cysteine residues that comprise the cysteine-rich repeat motifs in the extracellular domain are in bold.

DETAILED DESCRIPTION OF THE INVENTION

Figure 2A:
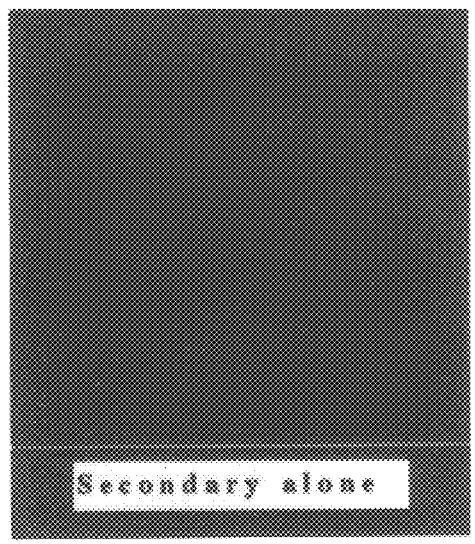
FIG. 2. OPG binding protein expression in COS-7 cells transfected with pcDNA/32D-F3. Cells were lipofected with pcDNA/32D-F3 DNA, the assayed for binding to either goat anti-human IgG1 alkaline phosphatase conjugate (secondary alone), human OPG[22-201]-Fc plus secondary (OPG-Fc), or a chimeric ATAR extracellular domain-Fc fusion protein (sATAR-Fc). ATAR is a new member of the TNFR superfamily, and the sATAR-Fc fusion protein serves as a control for both human IgG1 Fc domain binding, and generic TNFR releated protein, binding to 32D cell surface molecules.
Figure 2B:
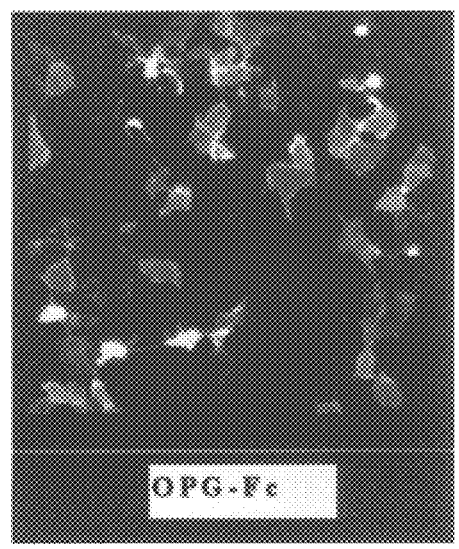
Figure 2C:
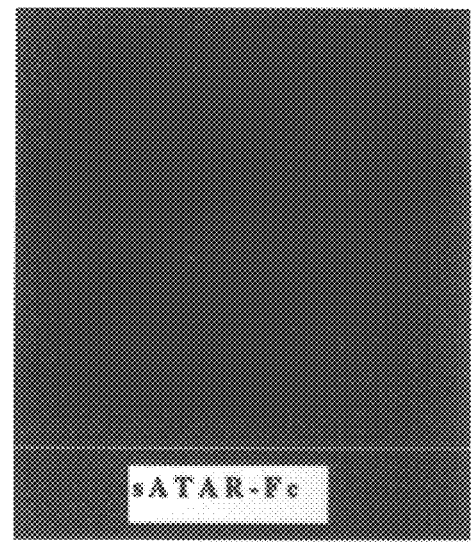

The invention provides for a polypeptide referred to as an OPG binding protein, which specficially binds OPG and is involved in osteoclast differentiation. A cDNA clone encoding the murine form of the polypeptide was identified from a library prepared from a mouse myelomonocytic cell line 32-D and transfected into COS cells. Transfectants were screened for their ability to bind to an OPG[22–201]-Fc fusion polypeptide (Example 1). The nucleic acid sequence revealed that OPG binding protein is a novel member of the TNF family and is most closely related to AGP-1, a polypeptide previously described in co-owned and co-pending U.S. Ser. No. 08/660,562, filed Jun. 7, 1996. (A polypeptide identical to AGP-1 and designated TRAIL is described in Wiley et al. Immunity 3, 673–682 (1995)). OPG binding protein is predicted be a type II transmembrane protein having a cytoplamsic domain at the amino terminus, a transmembrane domain, and a carboxy terminal extracellular domain (FIG. 1). The amino terminal cytoplasmic domain spans about residues 1–48, the transmembrane domain spans about residues 49–69 and the extracellular domain spans about residues 70–316 as shown in FIG. 1 (SEQ ID NO: 2). The membrane-associated protein specifically binds OPG (FIG. 2). Thus OPG binding protein and OPG share many characteristics of a receptor-ligand pair although it is possible that other naturally-occurring receptors for OPG binding protein exist.

A DNA clone encoding human OPG binding protein was isolated from a lymph node cDNA library. The human sequence (FIG. 4) is homologous to the murine sequence. Purified soluble murine OPG binding protein stimulated osteoclast formation in vitro and induced hypercalcemia and bone resorption in vivo.

OPG binding protein refers to a polypeptide having an amino acid sequence of mammalian OPG binding protein, or a fragment, analog, or derivative thereof, and having at least the activity of binding OPG. In preferred embodiments, OPG binding protein is of murine or human origin. In another embodiment, OPG binding protein is a soluble protein having, in one form, an isolated extracellular domain separate from cytoplasmic and transmembrane domains. OPG binding protein is involved in osteoclast differentiation and in the rate and extent of bone resorption, and was found to stimulate osteoclast formation and stimulate bone resorption.

Nucleic Acids

The invention provides for isolated nucleic acids encoding OPG binding proteins. As used herein, the term nucleic acid comprises cDNA, genomic DNA, wholly or partially synthetic DNA, and RNA. The nucleic acids of the invention are selected from the group consisting of:

a) the nucleic acids as shown in FIG. 1 (SEQ ID NO: 1) and FIG. 4 (SEQ ID NO: 3);

b) nucleic acids which hybridize to the polypeptide coding regions of the nucleic acids shown in FIG. 1 (SEQ ID NO: 1) and FIG. 4 (SEQ ID NO: 3); and remain hybridized to the nucleic acids under high stringency conditions; and c) nucleic acids which are degenerate to the nucleic acids of (a) or (b).

Nucleic acid hybridizations typically involve a multi-step process comprising a first hybridization step to form nucleic acid duplexes from single strands followed by a second hybridization step carried out under more stringent conditions to selectively retain nucleic acid duplexes having the desired homology. The conditions of the first hybridization step are generally not crucial, provided they are not of higher stringency than the second hybridization step. Generally, the second hybridization is carried out under conditions of high stringency, wherein "high stringency" conditions refers to conditions of temperature and salt which are about 12°–20° C. below the melting temperature ($T_m$) of a perfect hybrid of part or all of the complementary strands corresponding to FIG. 1 (SEQ. ID. NO: 2) and FIG. 4 (SEQ ID NO: 4) In one embodiment, "high stringency" conditions refer to conditions of about 65° C. and not more than about 1M Na+. It is understood that salt concentration, temperature and/or length of incubation may be varied in either the first or second hybridization steps such that one obtains the hybridizing nucleic acid molecules according to the invention. Conditions for hybridization of nucleic acids and calculations of $T_m$ for nucleic acid hybrids are described in Sambrook et al. *Molecular Cloning: A Laboratory Manual* Cold Spring Harbor Laboratory Press, New York (1989).

The nucleic acids of the invention may hybridize to part or all of the polypeptide coding regions of OPG binding protein as shown in FIG. 1 (SEQ ID NO: 2) and FIG. 4 (SEQ ID NO: 4); and 30 therefore may be truncations or extensions of the nucleic acid sequences shown therein. Truncated or extended nucleic acids are encompassed by the invention provided that they retain at least the property of binding OPG. In one embodiment, the nucleic acid will encode a polypeptide of at least about 10 amino acids. In another embodiment, the nucleic acid will encode a polypeptide of at least about 20 amino acids. In yet another embodiment, the nucleic acid will encode a polypeptide of at least about 50 amino acids. The hybridizing nucleic acids may also include noncoding sequences located 5' and/or 3' to the OPG binding protein coding regions. Noncoding sequences include regulatory regions involved in expression of OPG binding protein, such as promoters, enhancer regions, translational initiation sites, transcription termination sites and the like.

In preferred embodiments, the nucleic acids of the invention encode mouse or human OPG binding protein. Nucleic acids may encode a membrane bound form of OPG binding protein or soluble forms which lack a functional transmembrane region. The predicted transmembrane region for murine OPG binding protein includes amino acid residues 49–69 inclusive as shown in FIG. 1 (SEQ. ID. NO: 2). The predicted transmembrane region for human OPG binding protein includes residues 49–69 as shown in FIG. 4 (SEQ ID NO: 4). Substitutions which replace hydrophobic amino acid residues in this region with neutral or hydrophilic amino acid residues would be expected to disrupt membrane association and result in soluble OPG binding protein. In addition, deletions of part or all the transmembrane region would also be expected to produce soluble forms of OPG binding protein. Nucleic acids encoding amino acid residues 70–316 as shown in FIG. 1 (SEQ ID NO: 1), or fragments and analogs thereof, encompass soluble OPG binding proteins.

Nucleic acids encoding truncated forms of soluble human OPG binding proteins are also included. Soluble forms include residues 69–317 as shown in FIG. 4 (SEQ ID NO: 3) and truncations thereof. In one embodiment, N-terminal truncations generate polypeptides from residues, 70–317, 71–317, 72–317, and so forth. In another embodiment, nucleic acids encode soluble OPGbp comprising residues 69–317 and N-terminal truncations thereof up to OPGbp [158–317], or alternatively, up to OPGbp [166–317].

Plasmid phuOPGbp 1.1 in *E. coli* strain DH10 encoding human OPG binding protein was deposited with the American Type Culture Collection, Rockville, Md. on Jun. 13, 1997.

Nucleic acid sequences of the invention may be used for the detection of sequences encoding OPG binding protein in biological samples. In particular, the sequences may be used to screen cDNA and genomic libraries for related OPG binding protein sequences, especially those from other species. The nucleic acids are also useful for modulating levels of OPG binding protein by anti-sense technology or in vivo gene expression. Development of transgenic animals expressing OPG binding protein is useful for production of the polypeptide and for the study of in vivo biological activity.

Vectors and Host Cells

The nucleic acids of the invention will be linked with DNA sequences so as to express biologically active OPG binding protein. Sequences required for expression are known to those skilled in the art and include promoters and enhancer sequences for initiation of RNA synthesis, transcription termination sites, ribosome binding sites for the initiation of protein synthesis, and leader sequences for secretion. Sequences directing expression and secretion of OPG binding protein may be homologous, i.e., the sequences are identical or similar to those sequences in the genome involved in OPG binding protein expression and secretion, or they may be heterologous. A variety of plasmid vectors are available for expressing OPG binding protein in host cells (see, for example, methods in Enzymology v. 185, Goeddel, D. V. ed., Academic Press (1990)). For expression in mammalian host cells, a preferred embodiment is plasmid pDSRα described in PCT Application No. 90/14363. For expression in bacterial host cells, preferred embodiments include plasmids harboring the lux promoter (see co-owned and co-pending U.S. Ser. No. 08/577,778, filed Dec. 22, 1995). In addition, vectors are available for the tissue-specific expression of OPG binding protein in transgenic animals. Retroviral and adenovirus-based gene transfer vectors may also be used for the expression of OPG binding protein in human cells for in vivo therapy (see PCT Application No. 86/00922).

Procaryotic and eucaryotic host cells expressing OPG binding protein are also provided by the invention. Host cells include bacterial, yeast, plant, insect or mammalian cells. OPG binding protein may also be produced in transgenic animals such as mice or goats. Plasmids and vectors containing the nucleic acids of the invention are introduced into appropriate host cells using transfection or transformation techniques known to one skilled in the art. Host cells may contain DNA sequences encoding OPG binding protein as shown in FIG. 1 or a portion thereof, such as the extracellular domain or the cytoplasmic domain. Nucleic acids encoding OPG binding proteins may be modified by substitution of codons which allow for optimal expression in a given host. At least some of the codons may be so-called preference codons which do not alter the amino acid sequence and are frequently found in genes that are highly expressed. However, it is understood that codon alterations to optimize expression are not restricted to the introduction of preference codons. Examples of preferred mammalian host cells for OPG binding protein expression include, but are not limited to COS, CHOd-, 293 and 3T3 cells. A preferred bacterial host cell is *Escherichia coli*.

Polypeptides

The invention also provides OPG binding protein as the product of procaryotic or eucaryotic expression of an exogenous DNA sequence, i.e., OPG binding protein is recombinant OPG binding protein. Exogenous DNA sequences include cDNA, genomic DNA and synthetic DNA sequences. OPG binding protein may be the product of bacterial, yeast, plant, insect or mammalian cells expression, or from cell-free translation systems. OPG binding protein produced in bacterial cells will have an N-terminal methionine residue. The invention also provides for a process of producing OPG binding protein comprising growing procaryotic or eucaryotic host cells transformed or transfected with nucleic acids encoding OPG binding protein and isolating polypeptide expression products of the nucleic acids.

Polypeptides which are mamalian OPG binding proteins or are fragments, analogs or derivatives thereof are encompassed by the invention. In a preferred embodiment, the OPG binding protein is human OPG binding protein. A fragment of OPG binding protein refers to a polypeptide having a deletion of one or more amino acids such that the resulting polypeptide has at least the property of binding OPG. Said fragments will have deletions originating from the amino terminal end, the carboxy terminal end, and internal regions of the polypeptide. Fragments of OPG binding protein are at least about ten amino acids, at least about 20 amino acids, or at least about 50 amino acids in length. In preferred embodiments, OPG binding protein will have a deletion of one or more amino acids from the transmembrane region (amino acid residues 49–69 as shown in FIG. 1), or, alternatively, one or more amino acids from the amino-terminus up to and/or including the transmembrane region (amino acid residues 1–49 as shown in FIG. 1). In another embodiment, OPG binding protein is a soluble protein comprising, for example, amino acid residues 69–316, or 70–316, or N-terminal or C-terminal truncated forms thereof, which retain OPG binding activity. OPG binding protein is also a human soluble protein as shown in FIG. 4 comprising residues 69–317 as shown in FIG. 4 and N-terminal truncated forms thereof, e.g., 70–517, 71–517, 71–317, 72–317 and so forth. In a preferred embodiment, the soluble human OPG binding protein comprising residues 69–317 and N-terminal truncation thereof up to OPGbp [158–317], or alternatively up to OPG [166–317].

An analog of an OPG binding protein refers to a polypeptide having a substitution or addition of one or more amino acids such that the resulting polypeptide has at least the property of binding OPG. Said analogs will have substitutions or additions at any place along the polypeptide. Preferred analogs include those of soluble OPG binding proteins. Fragments or analogs may be naturally occurring, such as a polypeptide product of an allelic variant or a mRNA splice variant, or they may be constructed using techniques available to one skilled in the art for manipulating and synthesizing nucleic acids. The polypeptides may or may not have an amino terminal methionine residue.

Also included in the invention are derivatives of OPG binding protein which are polypeptides that have undergone post-translational modifications (e.g., addition of N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. In particular, chemically modified derivatives of OPG binding protein which provide additional advantages such as increased stability, longer circulating time, or decreased immunogenicity are contemplated. Of particular use is modification with water soluble polymers, such as polyethylene glycol and derivatives thereof (see for example U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties. Polypeptides may also be modified at pre-determined positions in the polypeptide, such as at the amino terminus, or at a selected lysine or arginine residue within the polypeptide. Other chemical modificaitons provided include a detectable label, such as an enzymatic, fluorescent, isotopic or affinity label to allow for detection and isolation of the protein.

OPG binding protein chimeras comprising part or all of an OPG binding protein amino acid sequence fused to a heterologous amino acid sequence are also included. The heterologous sequence may be any sequence which allows the resulting fusion protein to retain the at least the activity of binding OPG. In a preferred embodiment, the carboxy terminal extracellular domain of OPG binding protein is fused to a heterologous sequence. Such sequences include heterologous cytoplasmic domains that allow for alternative intracellular signalling events, sequences which promote oligomerization such as the Fc region of IgG, enzyme sequences which provide a label for the polypeptide, and sequences which provide affinity probes, such as an antigen-antibody recognition.

The polypeptides of the invention are isolated and purified from tissues and cell lines which express OPG binding protein, either extracted from lysates or from conditioned growth medium, and from transformed host cells expressing OPG binding protein. OPG binding protein may be obtained from murine myelomonocytic cell line 32-D (ATCC accession no. CRL-11346). Human OPG binding protein, or nucleic acids encoding same, may be isolated from human lymph node or fetal liver tissue. Isolated OPG binding protein is free from association with human proteins and other cell constituents.

A method for the purification of OPG binding protein from natural sources (e.g. tissues and cell lines which normally express OPG binding protein) and from transfected host cells is also encompassed by the invention. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-OPG binding protein antibody or biotin-streptavidin affinity complex and the like.

Antibodies

Antibodies specifically binding the polypeptides of the invention are also encompassed by the invention. The antibodies may be produced by immunization with full-length OPG binding protein, soluble forms of OPG binding protein, or a fragment thereof. The antibodies of the invention may be polyclonal or monoclonal, or may be recombinant antibodies, such as chimeric antibodies wherein the murine constant regions on light and heavy chains are replaced by human sequences, or CDR-grafted antibodies wherein only the complementary determining regions are of murine origin. Antibodies of the invention may also be human antibodies prepared, for example, by immunization of transgenic animals capable of producing human antibodies (see, for example, PCT Application No. WO93/12227). The antibodies are useful for detecting OPG binding protein in biological samples, thereby allowing the identification of cells or tissues which produce the protein In addition, antibodies which bind to OPG binding protein and block interaction with other binding compounds may have therapeutic use in modulating osteoclast differentiation and bone resorption.

Antibodies to the OPG binding protein may be useful in treatment of bone diseases such as, osteoporosis and Paget's disease. Antibodies can be tested for binding to the OPG binding protein in the absence or presence of OPG and examined for their ability to inhibit ligand (OPG binding protein) mediated osteoclastogenesis and/or bone resorption. It is also anticipated that the peptides themselves may act as an antagonist of the ligand: receptor interaction and inhibit ligand-mediated osteoclastogenesis, and peptides of the OPG binding protein will be explored for this purpose as well.

Compositions

The invention also provides for pharmaceutical compositions comprising a therapeutically effective amount of the OPG binding protein of the invention together with a pharmaceutically acceptable diluent, carrier, solubilizer, emulsifier, preservative and/or adjuvant. The invention also provides for pharmaceutical compositions comprising a therapeutically effective amount of an OPG binding protein agonist or antagonist. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Selection of a particular composition will depend upon a number of factors, including the condition being treated, the route of administration and the pharmacokinetic parameters desired. A more extensive survey of component suitable for pharmaceutical compositions is found in *Remington's Pharmaceutical Sciences,* 18th ed. A. R. Gennaro, ed. Mack, Easton, Pa. (1980).

In a preferred embodiment, compositions comprising soluble OPG binding proteins are also provided. Also encompassed are compositions comprising soluble OPG binding protein modified with water soluble polymers to increase solubility, stability, plasma half-life and bioavailability. Compositions may also comprise incorporation of soluble OPG binding protein into liposomes, microemulsions, micelles or vesicles for controlled delivery over an extended period of time. Soluble OPG binding protein may be formulated into microparticles suitable for pulmonary administration.

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the coding region of OPG binding protein and/or flanking regions to cells and tissues as part of an anti-sense therapy regimen.

Methods of Use

OPG binding proteins may be used in a variety of assays for detecting OPG and characterizing interactions with OPG. In general, the assay comprises incubating OPG binding protein with a biological sample containing OPG under conditions which permit binding to OPG to OPG binding protein, and measuring the extent of binding. OPG may be purified or present in mixtures, such as in body fluids or culture medium. Assays may be developed which are qualitative or quantitative, with the latter being useful for determining the binding parameters (affinity constants and kinetics) of OPG to OPG binding protein and for quantitating levels of biologically active OPG in mixtures. Assays may also be used to evaluate the binding of OPG to fragments, analogs and derivatives of OPG binding protein and to identify new OPG and OPG binding protein family members.

Binding of OPG to OPG binding protein may be carried out in several formats, including cell-based binding assays, membrane binding assays, solution-phase assays and immunoassays. In general, trace levels of labeled OPG are incubated with OPG binding protein samples for a specified period of time followed by measurement of bound OPG by filtration, electrochemiluminescent (ECL, ORIGEN system by IGEN), cell-based or immunoassays. Homogeneous assay technologies for radioactivity (SPA; Amersham) and time resolved fluoresence (HTRF, Packard) can also be implemented. Binding is detected by labeling OPG or an anti-OPG antibody with radioactive isotopes (125I, 35S, 3H), fluorescent dyes (fluorescein), lanthanide (Eu3+) chelates or cryptates, orbipyridyl-ruthenium (Ru2+) complexes. It is understood that the choice of a labeled probe will depend upon the detection system used. Alternatively, OPG may be modified with an unlabled epitope tag (e.g., biotin, peptides, $His_6$, myc) and bound to proteins such as streptavidin, anti-peptide or anti-protein antibodies which have a detectable label as described above.

In an alternative method, OPG binding protein may be assayed directly using polyclonal or monoclonal antibodies to OPG binding proteins in an immunoassay. Additional forms of OPG binding proteins containing epitope tags as described above may be used in solution and immunoassays.

Methods for indentifying compounds which interact with OPG binding protein are also encompassed by the invention. The method comprises incubating OPG binding protein with a compound under conditions which permit binding of the compound to OPG binding protein, and measuring the extent of binding. The compound may be substantially purified or present in a crude mixture. Binding compounds may be nucleic acids, proteins, peptides, carbohydrates, lipids or small molecular weight organic compounds. The compounds may be further characterized by their ability to increase or decrease OPG binding protein activity in order to determine whether they act as an agonist or an antagonist.

OPG binding proteins are also useful for identification of intracellular proteins which interact with the cytoplasmic domain by a yeast two-hybrid screening process. As an example, hybrid constructs comprising DNA encoding the N-terminal 50 amino acids of an OPG binding protein fused to a yeast GAL4-DNA binding domain may be used as a two-hybrid bait plasmid. Positive clones emerging from the screening may be characterized further to identify interacting proteins. This information may help elucidate a intracellular signaling mechanism associated with OPG binding protein and provide intracellular targets for new drugs that modulate bone resorption.

OPG binding protein may be used to treat conditions characterized by excessive bone density. The most common condition is osteopetrosis in which a genetic defect results in elevated bone mass and is usually fatal in the first few years of life. Osteopetrosis is preferably treated by administration of soluble OPG binding protein.

The invention also encompasses modulators (agonists and antagonists) of OPG binding protein and the methods for obtaining them. An OPG binding protein modulator may either increase or decrease at least one activity associated with OPG binding protein, such as ability to bind OPG or some other interacting molecule or to regulate osteoclast maturation. Typically, an agonist or antagonist may be a co-factor, such as a protein, peptide, carbohydrate, lipid or small molecular weight molecule, which interacts with OPG binding protein to regulate its activity. Potential polypeptide antagonists include antibodies which react with either soluble or membrane-associated forms of OPG binding protein, and soluble forms of OPG binding protein which comprise part or all of the extracellular domain of OPG binding protein. Molecules which regulate OPG binding protein expression typically include nucleic acids which are complementary to nucleic acids encoding OPG binding protein and which act as anti-sense regulators of expression.

OPG binding protein is involved in controlling formation of mature osteoclasts, the primary cell type implicated in bone resorption. An increase in the rate of bone resorption (over that of bone formation) can lead to various bone disorders collectively referred to as osteopenias, and include osteoporosis, osteomyelitis, hypercalcemia, osteopenia brought on by surgery or steroid administration, Paget's disease, osteonecrosis, bone loss due to rheumatoid arthritis; periodontal bone loss, immobilization, prosthetic loosing and osteolytic metastasis. Conversely, a decrease in the rate of bone resorption can lead to osteopetrosis, a condition marked by excessive bone density. Agonists and antagonists of OPG binding protein modulate osteoclast formation and may be administered to patients suffering from bone disorders. Agonists and antagonists of OPG binding protein used for the treatment of osteopenias may be administered alone or in combination with a therapeutically effective amount of a bone growth promoting agent including bone morphogenic factors designated BMP-1 to BMP-12, transforming growth factor-β and TGF-β family members, fibroblast growth factors FGF-1 to FGF-10, interleukin-1 inhibitors, TNFα inhibitors, parathyroid hormone, E series prostaglandins, bisphosphonates and bone-enhancing minerals such as fluoride and calcium. Antagonists of OPG binding proteins may be particularly useful in the treatment of osteopenia.

Receptors for Osteoprotegerin Binding Proteins

The invention also provides for receptors which interact with OPG binding proteins. More particularly, the invention provides for an osteoclast differentiation and activation receptor (ODAR). ODAR is a transmembrane polypeptide which shows highest degree of homology to CD40, a TNF receptor family member. The nucleic acid sequence of murine ODAR and encoded polypeptide is shown in FIG. 10. The human homolog of murine ODAR may be readily isolated by hybridization screening of a human cDNA or genomic library with the nucleic acid sequence of FIG. 10. Procedures for cloning human ODAR are similar to those described in Example 5 for cloning human OPG binding proteins. The human homolog of the polypeptide shown in FIG. 10 has appeared in Anderson et al. (Nature 390, 175–179 (1997)) and is referred to therein as RANK. RANK is characterized as a type I transmembrane protein having homology to TNF receptor family members and is involved in dendritic cell function.

Figure 13:
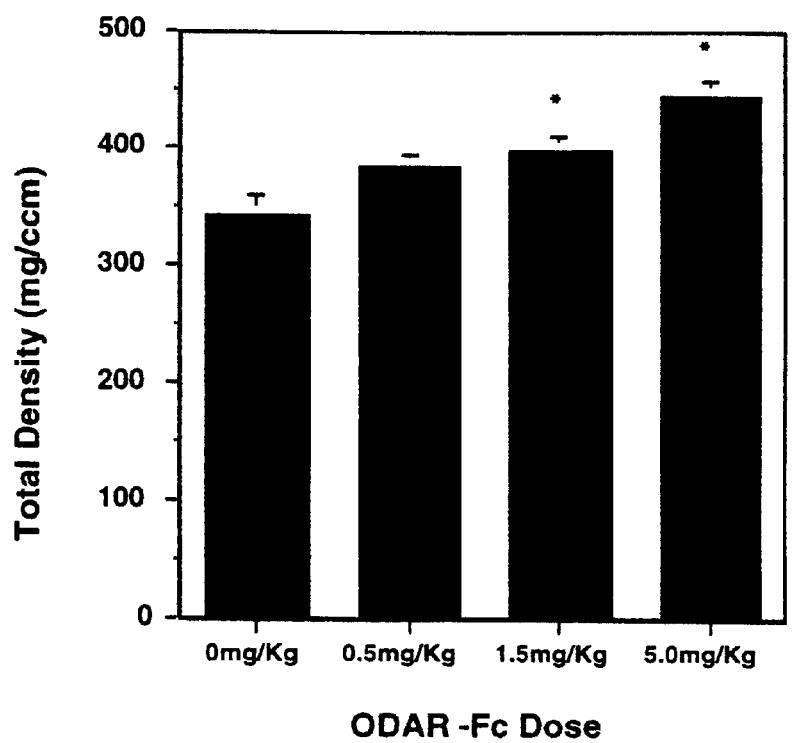
FIG. 13. Bone mineral density in mice after treatment for four days with ODAR-Fc at varying doses. Mice received ODAR-Fc by daily subcutaneous injection in a phosphate buffered saline vehicle. Mineral density was determined from bones fixed in 70% ETOH at the proximal tibial metaphysis mice by peripheral quantitative computed tomography (pQCT) (XCT-960M, Norland Medical Systems, Ft Atkinson, Wis.). Two 0.5 mm cross-sections of bone, 1.5 mm and 2.0 mm from the proximal end of the tibia were analyzed (XMICE 5.2, Stratec, Germany) to determine total bone mineral density in the metaphysis. A soft tissue separation threshold of 1500 was used to define the boundary of the metaphyseal bone. ODAR-Fc produced a significant increase in bone mineral density in the proximal tibial metaphysis in a dose dependent manner. Group n=4.

Evidence for the interaction of ODAR and OPG binding protein is shown in Example 13. A soluble form of ODAR (ODAR-Fc fusion protein) prevents osteoclast maturation in vitro (FIG. 12) and increases bone density in normal mice after subcutaneous injection (FIG. 13). The results are consistent with OPG binding protein interacting with and activating ODAR to promote osteoclast maturation.

Osteoclast development and the rate and extent of bone resorption are regulated by the interaction of OPG binding protein and ODAR. Compounds which decrease or block the interaction of OPG binding protein and ODAR are potential antagonists of OPG binding protein activity and may disrupt osteoclast development leading to decreased bone resorption. Alternatively, compounds which increase the interaction of OPG binding protein and ODAR are potential agonists which promote osteoclast development and enhance bone resorption.

A variety of assays may be used to measure the interaction of OPG binding protein and ODAR in vitro using purified proteins. These assays may be used to screen compounds for their ability to increase or decrease the rate or extent of binding to ODAR by OPG binding protein. In one type of assay, ODAR protein can be immobilized by attachment to the bottom of the wells of a microtiter plate. Radiolabeled OPG binding protein (for example, iodinated OPG binding protein) and the test compound(s) can then be added either one at a time (in either order) or simultaneously to the wells. After incubation, the wells can be washed and counted using a scintillation counter for radioactivity to determine the extent of binding to ODAR by OPG binding protein in the presence of the test compound. Typically, the compound will be tested over a range of concentrations, and a series of control wells lacking one or more elements of the test assays can be used for accuracy in evaluation of the results. An alternative to this method involves reversing the "positions" of the proteins, i.e., immobilizing OPG binding protein to the mictrotiter plate wells, incubating with the test compound and radiolabeled ODAR, and determining the extent of ODAR binding (see, for example, chapter 18 of *Current Protocols in Molecular Biology,* Ausubel et al., eds., John Wiley & Sons, New York, N.Y. [1995]).

As an alternative to radiolabelling, OPG binding protein or ODAR may be conjugated to biotin and the presence of biotinylated protein can then be detected using streptavidin linked to an enzyme, such as horse radish peroxidase [HRP] or alkaline phosphatase [AP], that can be detected colorometrically, or by fluorescent tagging of streptavidin. An antibody directed to OPG binding protein or ODAR that is conjugated to biotin may also be used and can be detected after incubation with enzyme-linked streptavidin linked to AP or HRP OPG binding protein and ODAR may also be immobilized by attachment to agarose beads, acrylic beads or other types of such inert substrates. The substrate-protein complex can be placed in a solution containing the complementary protein and the test compound; after incubation, the beads can be precipitated by centrifugation, and the amount of binding between OPG binding protein and ODAR can be assessed using the methods described above. Alternatively, the substrate-protein complex can be immobilized in a column and the test molecule and complementary protein passed over the column. Formation of a complex between OPG binding protein and ODAR can then be assessed using any of the techniques set forth above, i.e., radiolabeling, antibody binding, or the like.

Another type of in vitro assay that is useful for identifying a compound which increases or decreases formation of an ODAR/OPG binding protein complex is a surface plasmon resonance detector system such as the Biacore assay system (Pharmacia, Piscataway, N.J.). The Biacre system may be carried out using the manufacturer's protocol. This assay essentially involves covalent binding of either OPG binding protein or ODAR to a dextran-coated sensor chip which is located in a detector. The test compound and the other complementary protein can then be injected into the chamber containing the sensor chip either simultaneously or sequentially and the amount of complementary protein that binds can be assessed based on the change in molecular mass which is physically associated with the dextran-coated side of the of the sensor chip; the change in molecular mass can be measured by the detector system.

In some cases, it may be desirable to evaluate two or more test compounds together for use in increasing or decreasing formation of ODAR/OPG binding protein complex. In these cases, the assays set forth above can be readily modified by adding such additional test compound(s) either simultaneously with, or subsequently to, the first test compound. The remainder of steps in the assay are as set forth above.

In vitro assays such as those described above may be used advantageously to screen rapidly large numbers of compounds for effects on complex formation by ODAR and OPG binding protein. The assays may be automated to screen compounds generated in phage display, synthetic peptide and chemical synthesis libraries.

Compounds which increase or decrease complex formation of OPG binding protein and ODAR may also be screened in cell culture using ODAR-bearing cells and cell lines. Cells and cell lines may be obtained from any mammal, but preferably will be from human or other primate, canine, or rodent sources. ODAR containing cells such as osteoclasts may be enriched from other cell types by affinity chromatography using publicly available procedures. Attachment of OPG binding protein to ODAR-bearing cells is evaluated in the presence or absence of test compounds and the extent of binding may be determined by, for example, flow cytometry using a biotinylated antibody to OPG binding protein. Alternatively, a mouse or human osteoclast culture may be established as described in Example 8 and test compounds may be evaluated for their ability to block osteoclast maturation stimulated by addition of CSF-1 and OPG binding protein. Cell culture assays may be used advantageously to further evaluate compounds that score positive in protein binding assays described above.

Compounds which increase or decrease the interaction of OPG binding protein with ODAR may also be evaluated for in vivo activity by administration of the compounds to mice followed by measurements of bone density using bone scanning densitometry or radiography. Procedures for measuring bone density are described in PCT publication WO97/23614 and in Example 13.

The invention provides for compounds which decrease or block the interaction of OPG binding protein and ODAR and are antagonists of osteoclast formation. Such compounds generally fall into two groups. One group includes those compounds which are derived from OPG binding protein or which interact with OPG binding protein. These have been described above. A second group includes those compounds which are derived from ODAR or which interact with ODAR. Examples of compounds which are anatagonists of ODAR include nucleic acids, proteins, peptides, carbohydrates, lipids or small molecular weight organic compounds.

Antagonists of ODAR may be compounds which bind at or near one or more binding sites for OPG bp in the ODAR extracellular domain and decrease or completely block complex formation. Those regions on ODAR that are involved in complex formation with OPG binding protein may be identified by analogy with the structure of the homologous TNFβ/TNF-R55 complex which has been described in Banner et al. (Cell 73, 431–445 (1993)). For example, the structure of the TNFβ/TNF-R55 complex may be used to identify regions of OPG binding protein and ODAR that are involved in complex formation. Compounds may then be designed which preferentially bind to the regions involved in complex formation and act as antagonists. In one approach set forth in Example 11, peptide antigens were designed for use in raising antibodies to OPG binding protein that act as antagonists. These antibodies are expected to bind to OPG binding protein and block complex formation with ODAR. In a similar approach, peptide antigens based upon ODAR structure may be used to raise anti-ODAR antibodies that act as antagonists.

Anatoginists of ODAR may also bind to ODAR at locations distinct from the binding site(s) for OPG bp and induce conformational changes in ODAR polypeptide that result in decreased or nonproductive complex formation with OPG binding proteins.

In one embodiment, an antagonist is a soluble form of ODAR lacking a functional transmembrane domain. Soluble forms of ODAR may have a deletion of one or more amino acids in the transmembrane domain (amino acids 214–234 as shown in FIG. 10). Soluble ODAR polypeptides may have part or all of the extracellular domain and are capable of binding OPG binding protein. Optionally, soluble ODAR may be part of a chimeric protein, wherein part or all of the extracellular domain of ODAR is fused to a heterologous amino acid sequence. In one embodiment, the heterologous amino acid sequence is an Fc region from human IgG.

Modulators (agonists and antagonists) of ODAR may be used to prevent or treat osteopenia, including osteoporosis, osteomyelitis, hypercalcemia of malignancy, osteopenia brought on by surgery or steroid administration, Paget's disease, osteonecrosis, bone loss due to rheumatoid arthritis, periodontal bone loss, immobilization, prosthetic loosing and osteolytic metastasis. Agonists and antagonists of ODAR used for the treatment of osteopenias may be administered alone or in combination with a therapeutically effective amount of a bone growth promoting agent including bone morphogenic factors designated BMP-1 to BMP-12, transforming growth factor-β and TGF-β family members, fibroblast growth factors FGF-1 to FGF-10, interleukin-1 inhibitors, TNFα inhibitors, parathyroid hormone, E series prostaglandins, bisphosphonates, estrogens, SERMs and bone-enhancing minerals such as fluoride and calcium. Antagonists of ODAR are particularly useful in the treatment of osteopenia.

The following examples are offered to more fully illustrate the invention, but are not construed as limiting the scope thereof.

EXAMPLE 1

Identification of a cell line source for an OPG binding protein

Osteoprotegerin (OPG) negatively regulates osteoclastogenesis in vitro and in vivo. Since OPG is a TNFR-related protein, it is likely to interact with a TNF-related family member while mediating its effects. With one exception, all known members of the TNF superfamily are type II transmembrane proteins expressed on the cell surface. To identify a source of an OPG binding protein, recombinant OPG-Fc fusion proteins were used as immunoprobes to screen for OPG binding proteins located on the surface of various cell lines and primary hematopoietic cells.

Cell lines that grew as adherent cultures in vitro were treated using the following methods: Cells were plated into 24 well tissue culture plates (Falcon), then allowed to grow to approxiamtely 80% confluency. The growth media was then removed, and the adherent cultures were washed with phosphate buffered saline (PBS) (Gibco) containing 1% fetal calf serum (FCS). Recombinant mouse OPG [22–194]-Fc and human OPG [22–201]-Fc fusion proteins (see U.S. Ser. No. 08/706,945 filed Sep. 3, 1996) were individually diluted to 5 ug/ml in PBS containing 1% FCS, then added to the cultures and allowed to incubate for 45 min at 0° C. The OPG-Fc fusion protein solution was discarded, and the cells were washed in PBS-FCS solution as described above. The cultures were then exposed to phycoeyrthrin-conguated goat F(ab') anti-human IgG secondary antibody (Southern Biotechnology Associates Cat. # 2043-09) diluted into PBS-FCS. After a 30–45 min incubation at 0° C., the solution was discarded, and the cultures were washed as described above. The cells were then analysed by immunofluorescent microscopy to detect cell lines which express a cell surface OPG binding protein.

Suspension cell cultures were analysed in a similar manner with the following modifications: The diluent and wash buffer consisted of calcium- and magnesium-free phosphate buffered saline containing 1% FCS. Cells were harvested from exponentially replicating cultures in growth media, pelleted by centrifugation, then resuspended at $1\times10^7$ cells/ml in a 96 well microtiter tissue culture plate (Falcon). Cells were sequentially exposed to recombinant OPG-Fc fusion proteins, then secondary antibody as described above, and the cells were washed by centrifugation between each step. The cells were then analysed by fluorescence activated cell sorting (FACS) using a Becton Dickinson FACscan.

Using this approach, the murine myelomonocytic cell line 32D (ATCC accession no. CRL-11346) was found to express a surface molecule which could be detected with both the mouse OPG[22–194]-Fc and the human OPG [22–201]-Fc fusion proteins. Secondary antibody alone did not bind to the surface of 32D cells nor did purified human IgG1 Fc, indicating that binding of the OPG-Fc fusion proteins was due to the OPG moiety. This binding could be competed in a dose dependent manner by the addition of recombinant murine or human OPG[22–401] protein. Thus the OPG region required for its biological activity is capable of specifically binding to a 32D-derived surface molecule.

EXAMPLE 2

Expression cloning of a murine OPG binding protein

A cDNA library was prepared from 32D mRNA, and ligated into the mammalian expression vector pcDNA3.1(+) (Invitrogen, San Diego, Calif.). Exponentially growing 32D cells maintained in the presence of recombinant interleukin-3 were harvested, and total cell RNA was purified by acid guanidinium thiocyanate-phenol-chloroform extraction (Chomczynski and Sacchi. Anal. Biochem. 162, 156–159, (1987)). The poly (A+) mRNA fraction was obtained from the total RNA preparation by adsorption to, and elution from, Dynabeads Oligo (dT)25 (Dynal Corp) using the manufacturer's recommended procedures. A directional, oligo-dT primed cDNA library was prepared using the Superscript Plasmid System (Gibco BRL, Gaithersburg, Md.) using the manufacturer's recommended procedures. The resulting cDNA was digested to completion with Sal I and Not I restriction endonuclease, then fractionated by size exclusion gel chromatography. The highest molecular weight fractions were selected, and then ligated into the polyliker region of the plasmid vector pcDNA3.1(+) (Invitrogen, San Diego, Calif.). This vector contains the CMV promotor upstream of multiple cloning site, and directs high level expression in eukaryotic cells. The library was then electroporated into competent *E. coli* (ElectroMAX DH10B, Gibco, N.Y.), and titered on LB agar containing 100 ug/ml ampicillin. The library was then arrayed into segregated pools containing approximately 1000 clones/pool, and 1.0 ml cultures of each pool were grown for 16–20 hr at 37° C. Plasmid DNA from each culture was prepared using the Qiagen Qiawell 96 Ultra Plasmid Kit (catalog #16191) following manufacturer's recommended procedures.

Arrayed pools of 32D cDNA expression library were individually lipofected into COS-7 cultures, then assayed for the acquisition of a cell surface OPG binding protein. To do this, COS-7 cells were plated at a density of $1 \times 10^6$ per ml in six-well tissue culture plates (Costar), then cultured overnight in DMEM-(Gibco) containing 10% FCS. Approximately 2 µg of plasmid DNA from each pool was diluted into 0.5 ml of serum-free DMEM, then sterilized by centrifugation through a 0.2 µm Spin-X column (Costar). Simultaneously, 10 µl of Lipofectamine (Life Technologies Cat # 18324-012) was added to a separate tube containing 0.5 ml of serum-free DMEM. The DNA and Lipofectamine solutions were mixed, and allowed to incubate at RT for 30 min. The COS-7 cell cultures were then washed with serum-free DMEM, and the DNA-lipofectamine complexes were exposed to the cultures for 2–5 hr at 37° C. After this period, the media was removed, and replaced with DMEM containing 10% FCS. The cells were then cultured for 48 hr at 37° C.

To detect cultures that express an OPG binding protein, the growth media was removed, and the cells were washed with PBS-FCS solution. A 1.0 ml volume of PBS-FCS containing 5 µg/ml of human OPG[22–201]-Fc fusion protein was added to each well and incubated at RT for 1 hr. The cells were washed three times with PBS-FCS solution, and then fixed in PBS containing 2% paraformaldehyde and 0.2% glutaraldehyde in PBS at RT for 5 min. The cultures were washed once with PBS-FCS, then incubated for 1 hr at 65° C. while immersed in PBS-FCS solution. The cultures were allowed to cool, and the PBS-FCS solution was aspirated. The cultures were then incubated with an alkaline-phosphatase conjugated goat anti-human IgG (Fc specific) antibody (SIGMA Product # A-9544) at Rt for 30 min, then washed three-times with 20 mM Tris-Cl (pH 7.6), and 137 mM NaCl. Immune complexes that formed during these steps were detected by assaying for alkaline phosphatase activity using the Fast Red TR/AS-MX Substrate Kit (Pierce, Cat. # 34034) following the manufacturer's recommended procedures.

Using this approach, a total of approximately 300,000 independent 32D cDNA clones were screened, represented by 300 transfected pools of 1000 clones each. A single well was identifed that contained cells which acquired the ability to be specifically decorated by the OPG-Fc fusion protein. This pool was subdivided by sequential rounds of sib selection, yeilding a single plasmid clone 32D-F3 (FIG. 1). 32D-F3 plasmid DNA was then transfected into COS-7 cells, which were immunostained with either FITC-conjugated goat anti-human IgG secondary antibody alone, human OPG[22–201]-Fc fusion protein plus secondary, or with ATAR-Fc fusion protein (ATAR also known as HVEM; Montgomery et al. Cell 87, 427–436 (1996)) (FIG. 2). The secondary antibody alone did not bind to COS-7/32D-F3 cells, nor did the ATAR-Fc fusion protein. Only the OPG Fc fusion protein bound to the COS-7/32D-F3 cells, indicating that 32D-F3 encoded an OPG binding protein displayed on the surface of expressing cells.

EXAMPLE 3

OPG Binding Protein Sequence

The 32D-F3 clone isolated above contained an approximately 2.3 kb cDNA insert (FIG. 1), which was sequenced in both directions on an Applied Biosystems 373A automated DNA sequencer using primer-driven Taq dye-terminator reactions (Applied Biosystems) following the manufacturer's recommended procedures. The resulting nucleotide sequence obtained was compared to the DNA sequence database using the FASTA program (GCG, Univeristy of Wisconsin), and analysed for the presence of long open reading frames (LORF's) using the "Six-way open reading frame" application (Frames) (GCG, Univeristy of Wisconsin). A LORF of 316 amino acid (aa) residues beginning at methionine was detected in the appropriate orientation, and was preceded by a 5' untranslated region of about 150 bp. The 5' untranslated region contained an in-frame stop codon upstream of the predicted start codon. This indicates that the structure of the 32D-F3 plasmid is consistent with its ability to utilize the CMV promotor region to direct expression of a 316 aa gene product in mammalian cells.

The predicted OPG binding protein sequence was then compared to the existing database of known protein sequences using a modified version of the FASTA program (Pearson, Meth. Enzymol. 183, 63–98 (1990)). The amino acid sequence was also analysed for the presence of specific motifs conserved in all known members of the tumor necrosis factor (TNF) superfamily using the sequence profile method of (Gribskov et al. Proc. Natl. Acad. Sci. USA 83, 4355–4359 (1987)), as modified by Luethy et al. Protein Sci. 3, 139–146 (1994)). There appeared to be significant homology throughout the OPG binding protein to several members of the TNF superfamily. The mouse OPG binding protein appear to be most closely related to the mouse and human homologs of both TRAIL and CD40 ligand. Further analysis of the OPG binding protein sequence indicated a strong match to the TNF superfamily, with a highly significant Z score of 19.46.

The OPG binding protein amino acid sequence contains a probable hydrophobic transmembrane domain that begins at a M49 and extends to L69. Based on this configuration relative to the methionine start codon, the OPG binding protein is predicted to be a type II transmembrane protein, with a short N-terminal intracellular domain, and a longer C-terminal extracellular domain (FIG. 4). This would be similar to all known TNF family members, with the exception of lymphotoxin alpha (Nagata and Golstein, Science 267, 1449–1456 (1995)).

EXAMPLE 4

Expression of human OPG binding protein mRNA

Multiple human tissue northern blots (Clontech, Palo Alto, Calif.) were probed with a $^{32}$P-dCTP labelled 32D-F3 restriction fragment to detect the size of the human transcript and to determine patterns of expression. Northern blots were prehybridized in 5 X SSPE, 50% formamide, 5 X Denhardt's solution, 0.5% SDS, and 100 µg/ml denatured salmon sperm DNA for 2–4 hr at 42° C. The blots were then hybridized in 5 X SSPE, 50% formamide, 2 X Denhardt's solution, 0.1% SDS, 100 µg/ml denatured salmon sperm DNA, and 5 ng/ml labelled probe for 18–24 hr at 42° C. The blots were then washed in 2 X SSC for 10 min at RT, 1 X SSC for 10 min at 50° C., then in 0.5 X SSC for 10–15 min.

Figure 3:
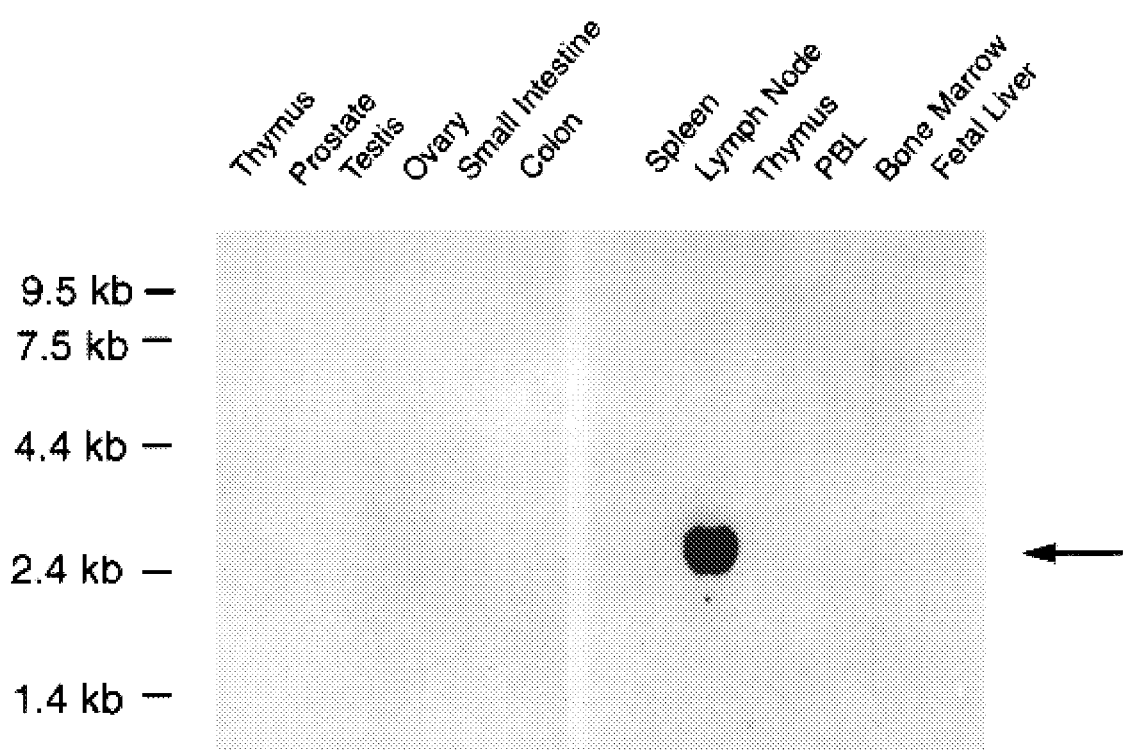
FIG. 3. Expression of OPG binding protein in human tissues. Northern blot analysis of human tissue mRNA (Clontech) using a radiolabeled 32D-F3 derived hybridization probe. Relative molecular mass is indicated at the left in kilobase pairs (kb). Arrowhead on right side indicates the migration of an approximately 2.5 kb transcript detected in lymph node mRNA. A very faint band of the same mass is also detected in fetal liver.

Using a probe derived from the mouse cDNA and hybridization under stringent conditions, a predominant mRNA species with a relative molecular mass of about 2.5 kb was detected in lymph nodes (FIG. 3). A faint signal was also detected at the same relative molecular mass in fetal liver mRNA. No OPG binding protein transcripts were detected in the other tissues examined. The data suggest that expression of OPG binding protein mRNA was extremely restricted in human tissues. The data also indicate that the cDNA clone isolated is very close to the size of the native transcript, suggesting 32D-F3 is a full length clone.

EXAMPLE 5

Molecular cloning of the human OPG binding protein

The human homolog of the OPG binding protein is expressed as an approximately 2.5 kb mRNA in human peripheral lymph nodes and is detected by hybridization with a mouse cDNA probe under stringent hybridization conditions. DNA encoding human OPG binding protein is obtained by screening a human lymph node cDNA library by either recombinant bacteriphage plaque, or transformed bacterial colony, hybridiziation methods (Sambrook et al. *Molecular Cloning: A Laboratory Manual* Cold Spring Harbor Press, N.Y. (1989)). To this the phage or plasmid cDNA library are screened using radioactively-labeled probes derived from the murine OPG binding protein clone 32D-F3. The probes are used to screen nitrocellulose filter lifted from a plated library. These filters are prehybridized and then hybridized using conditions specified in Example 4, ultimately giving rise to purified clones of the human OPG binding protein cDNA. Inserts obtained from any human OPG binding protein clones would be sequenced and analysed as described in Example 3.

A human lymph node poly A+ RNA (Clontech, Inc., Palo Alto, Calif.) was analysed for the presence of OPG-bp transcripts as previously in U.S. Ser. No. 08/577,788, filed Dec. 22, 1995. A northern blot of this RNA sample probed under stringent conditions with a 32P-labeled mouse OPG-bp probe indicated the presence of human OPG-bp transcripts. An oligo dT-primed cDNA library was then synthesized from the lymph node mRNA using the SuperScript kit (GIBCO life Technologies, Gaithersberg, Md.) as described in example 2. The resulting cDNA was size selected, and the high molecular fraction ligated to plasmid vector pcDNA 3.1 (+) (Invitrogen, San Diego, Calif.). Electrocompetent *E. coli* DH10 (GIBCO life Technologies, Gaithersberg, Md.) were transformed, and 1×10$^6$ ampicillin resistant transformants were screened by colony hybridization using a 32P-labeled mouse OPG binding protein probe.

A plasmid clone of putative human OPG binding protein cDNA was isolated, phuOPGbp-1.1, and contained a 2.3 kp insert. The resulting nucleotide sequence of the phuOPGbp-1.1 insert was approximately 80–85% homologous to the mouse OPG binding protein cDNA sequence. Translation of the insert DNA sequence indicated the presence of a long open reading frame predicted to encode a 317 aa polypeptide (FIG. 4). Comparison of the mouse and human OPG-bp polypeptides shows that they are ~87% identical, indicating that this protein is highly conserved during evolution.

The human OPG binding protein DNA and protein sequences were not present in Genbank, and there were no homologus EST sequences. As with the murine homolog, the human OPG binding protein shows strong sequence similarity to all members of the TNFα superfamily of cytokines.

EXAMPLE 6

Cloning and Bacterial Expression of OPG binding protein

PCR amplification employing the primer pairs and templates described below are used to generate various forms of murine OPG binding proteins. One primer of each pair introduces a TAA stop codon and a unique XhoI or SacII site following the carboxy terminus of the gene. The other primer of each pair introduces a unique NdeI site, a N-terminal methionine, and optimized codons for the amino terminal portion of the gene. PCR and thermocycling is performed using standard recombinant DNA methodology. The PCR products are purified, restriction digested, and inserted into the unique NdeI and XhoI or SacII sites of vector pAMG21 (ATCC accession no. 98113) and transformed into the prototrophic *E. coli* 393 or 2596. Other commonly used *E. coli* expression vectors and host cells are also suitable for expression. After transformation, the clones are selected, plasmid DNA is isolated and the sequence of the OPG binding protein insert is confirmed.

pAMG21-Murine OPG binding protein [75–316]

This construct was engineered to be 242 amino acids in length and have the following N-terminal and C-terminal residues, NH$_2$-Met(75)-Asp-Pro-Asn-Arg-Gln-Asp-Ile-Asp (316) —COOH. The template to be used for PCR was pcDNA/32D-F3 and oligonucleotides #1581-72 and #1581-76 were the primer pair to be used for PCR and cloning this gene construct.

1581-72:

5'-GTTCTCCTCATATGGATCCAAACCGTATTTCT GAAGACAGCACTCACTGCTT-3' (SEQ ID NO: 5)

1581-76:

5'-TACGCACTCCGCGGTTAGTCTATGTCCTGAA CTTTGA-3' (SEQ ID NO: 6)

pAMG21-Murine OPG binding protein [95–316]

This construct was engineered to be 223 amino acids in length and have the following N-terminal and C-terminal residues, NH$_2$-Met-His(95)-Glu-Asn-Ala-Gly-Gln-Asp-Ile-Asp(316) —COOH. The template used for PCR was pcDNA/32D-F3 and oligonucleotides #1591-90 and #1591-95 were the primer pair used for PCR and cloning this gene construct.

1591-90:

5'-ATTTGATTCTAGAAGGAGGAATAACATATG CATGAAAACGCAGGTCTGCAG-3' (SEQ ID NO: 7)

1591-95:

5'-TATCCGCGGATCCTCGAGTTAGTCTATGTC CTGAACTTTGAA-3' (SEQ ID NO: 8)

pAMG21-Murine OPG binding protein [107–316]

This construct was engineered to be 211 amino acids in length and have the following N-terminal and C-terminal residues, NH$_2$-Met-Ser(107)-Glu-Asp-Thr-Leu-Gln-Asp-Ile-Asp(316) —COOH. The template used for PCR was pcDNA/32D-F3 and oligonucleotides #1591-93 and #1591-95 were the primer pair used for PCR and cloning this gene construct.

1591-93:

5'-ATTTGATTCTAGAAGGAGGAATAACATATGT CTGAAGACACTCTGCCGGACTCC-3' (SEQ ID NO: 9)

1591-95:

5'-TATCCGCGGATCCTCGAGTTAGTCTATGTCC TGAACTTTGAA-3' (SEQ ID NO: 10)

pAMG21-Murine OPG binding protein [118–316]

This construct was engineered to be 199 amino acids in length and have the following N-terminal and C-terminal residues, NH$_2$-Met(118)-Lys-Gln-Ala-Phe-Gln-Gln-Asp-Ile-Asp(316)—COOH. The template used for PCR was pcDNA/32D-F3 and oligonucleotides #1591-94 and #1591-95 were the primer pair used for PCR and cloning this gene construct.

1591-94:
5'-ATTTGATTCTAGAAGGAGGAATAACATATG AAACAAGCTTTTCAGGGG-3' (SEQ ID NO: 11)

1591-95:
5'-TATCCGCGGATCCTCGAGTTAGTCTATGTCC TGAACTTTGAA-3'(SEQ ID NO: 12)

pAMG21-Murine OPG binding protein [128–316]

This construct was engineered to be 190 amino acids in length and have the following N-terminal and C-terminal residues, NH$_2$-Met-Lys(128)-Glu-Leu-Gln-His-Gln-Asp-Ile-Asp(316)—COOH. The template used for PCR was pcDNA/32D-F3 and oligonucleotides #1591-91 and #1591-95 were the primer pair used for PCR and cloning this gene construct.

1591-91:
5'-ATTTGATTCTAGAAGGAGGAATAACATATG AAAGAACTGCAGCACATTGTG-3' (SEQ ID NO: 13)

1591-95:
5'-TATCCGCGGATCCTCGAGTTAGTCTATGTCCT GAACTTTGAA-3' (SEQ ID NO: 14)

pAMG21-Murine OPG binding protein [137–316]

This construct was engineered to be 181 amino acids in length and have the following N-terminal and C-terminal residues, NH$_2$-Met-Gln(137)-Arg-Phe-Ser-Gly-Gln-Asp-Ile-Asp(316)—COOH. The template used for PCR was pcDNA/32D-F3 and oligonucleotides #1591-92 and #1591-95 were the primer pair used for PCR and cloning this genie construct.

1591-92:
5'-ATTTGATTCTAGAAGGAGGAATAACATATGCA GCGTTTCTCTGGTGCTCCA-3' (SEQ ID NO: 15)

1591-95:
5'-TATCCGCGGATCCTCGAGTTAGTCTATGTCC TGAACTTTGAA-3' (SEQ ID NO: 16)

pAMG21-Murine OPG binding Protein [146–316]

This construct is engineered to be 171 amino acids in length and have the following N-terminal and C-terminal residues, NH$_2$-Met (146)-Glu-Gly-Ser-Trp-Gln-Asp-Ile-Asp(316)—COOH. The template to be used for PCR is pAMG21-murine OPG binding protein [75–316] described above and oligonucleotides #1600-98 and #1581-76 will be the primer pair to be used for PCR and cloning this gene construct.

1600-98:
5'- GTTCTCCTCATATGGAAGGTTCTTGGTTGGA TGTGGCCCA-3' (SEQ ID NO: 17)

1581-76:
5'-TACGCACTCCGCGGTTAGTCTATGTCCTGA ACTTTGA-3' (SEQ ID NO: 18)

pAMG21-Murine OPG binding protein [156–316]

This construct is engineered to be 162 amino acids in length and have the following N-terminal and C-terminal residues, NH$_2$-Met-Arg(156)-Gly-Lys-Pro-Gln-Asp-Ile-Asp (316)—COOH. The template to be used for PCR is pAMG21-murine OPG binding protein [158–316] below and oligonucleotides #1619-86 and #1581-76 will be the primer pair to be used for PCR and cloning this gene construct.

1619-86:
5'- GTTCTCCTCATATGCGTGGTAAACCTGAAG CTCAACCATTTGCA-3' (SEQ ID NO: 19)

1581-76:
5'-TACGCACTCCGCGGTTAGTCTATGTCCTGAA CTTTGA-3' (SEQ ID NO: 20)

pAMG21-Murine OPG binding protein [158–316]

This construct was engineered to be 160 amino acids in length and have the following N-terminal and C-terminal residues, NH$_2$-Met-Lys(158)-Pro-Glu-Ala-Gln-Asp-Ile-Asp (316)—COOH. The template to be used for PCR was pcDNA/32D-F3 and oligonucleotides #1581-73 and #1581-76 were the primer pair to be used for PCR and cloning this gene construct.

1581-73:
5'-GTTCTCCTCATATGAAACCTGAAGCTCAAC CATTTGCACACCTCACCATCAAT-3' (SEQ ID NO: 21)

1581-76:
5'-TACGCACTCCGCGGTTAGTCTATGTCCTGA ACTTTGA-3' (SEQ ID NO: 22)

pAMG21-Murine OPG binding protein [166–316]

This construct is engineered to be 152 amino acids in length and have the following N-terminal and C-terminal residues, NH$_2$-Met-His(166)-Leu-Thr-Ile-Gln-Asp-Ile-Asp(316)—COOH. The template to be used for PCR is pcDNA/32D-F3 and oligonucleotides #1581-75 and #1581-76 will be the primer pair to be used for PCR and cloning this gene construct.

1581-75:
5'-GTTCTCCTCATATGCATTTAACTATTAACGC TGCATCTATCCCAT CGGGTTCCCATAAAGTCACT-3' (SEQ ID NO: 23)

1581-76:
5'-TACGCACTCCGCGGTTAGTCTATGTCCTGA ACTTTGA-3' (SEQ ID NO: 24)

pAMG21-Murine OPG binding protein [168–316]

This construct is engineered to be 150 amino acids in length and have the following N-terminal and C-terminal residues, NH$_2$-Met-Thr(168)-Ile-Asn-Ala-Gln-Asp-Ile-Asp (316)—COOH. The template to be used for PCR is pcDNA/32D-F3 and oligonucleotides #1581-74 and #1581-76 will be the primer pair to be used for PCR and cloning.

1581-74:
5'-GTTCTCCTCATATGACTATTAACGCTGCATC TATCCCATCGGGTTCCCATAAAGTCACT-3' (SEQ ID NO: 25)

1581-76:
5'-TACGCACTCCGCGGTTAGTCTATGTCCTGAA CTTTGA-3' (SEQ ID NO: 26)

It is understood that the above constructs are examples and one skilled in the art may readily obtain other forms of OPG binding protein using the general methodology presented her.

Recombinant bacterial constructs pAMG21-murine OPG binding protein [75–316], [95–316], [107–316], [118–316], [128–316], [137–316], and [158–316] have been cloned, DNA sequence confirmed, and levels of recombinant gene product expression following induction has been examined. All constructs produced levels of recombinant gene product which was readily visible following SDS polyacrylamide gel electrophoresis and coomassie staining of crude lysates. Growth of transformed E. coli 393 or 2596, induction of OPG binding protein expression and isolation of inclusion bodies containing OPG binding protein is done according to procedures described in PCT WO97/23614. Purification of OPG binding proteins from inclusion bodies requires solubilization and renaturing of OPG binding protein using procedures available to one skilled in the art. Recombinant murine OPG binding protein [158–316] was found to be produced mostly insolubly, but about 40% was found in the soluble fraction. Recombinant protein was purified from the soluble fraction as described below and its bioactivity examined.

EXAMPLE 7

Purification of recombinant murine OPG binding protein [158–316]

Frozen bacterial cells harboring expressed murine OPG binding protein (158–316) were thawed and resuspended in 20 mM tris-HCl pH 7.0, 10 mM EDTA. The cell suspension (20% w/v) was then homogenized by three passes through a microfluidizer. The lysed cell suspension was centrifuged in a JA14 rotor at 10,000 rpm for 45 minutes. SDS-PAGE analysis showed a band of approximately 18 kd molecular weight present in both inclusion bodies and the supernatant. The soluble fraction was then applied to a Pharmacia SP Sepharose 4 FF column equilibrated with 10 mM MES pH 6.0. The OPG binding protein was eluted with a 20 column volume gradient of 0–0.4M NaCl in MES pH 6.0. Fractions containing OPG binding protein were then applied to an ABX Bakerbond column equilibrated with 20 mM MES pH 6.0. OPG binding protein was eluted with a 15 CV gradient of 0–0.5M NaCl in MES pH 6.0. The final product was over 95% homogeneous by SDS-PAGE. N-terminal sequencing gave the following sequence: Met-Lys-Pro-Glu-Ala-Gln-Pro-Phe-Ala-His which was identified to that predicted for a polypeptide starting at residue 158 (with an initiator methionine). The relative molecular weight of the protein during SDS-PAGE does not change upon reduction.

EXAMPLE 8

In vitro bioactivity of recombinant soluble OPG binding protein

Figure 5:
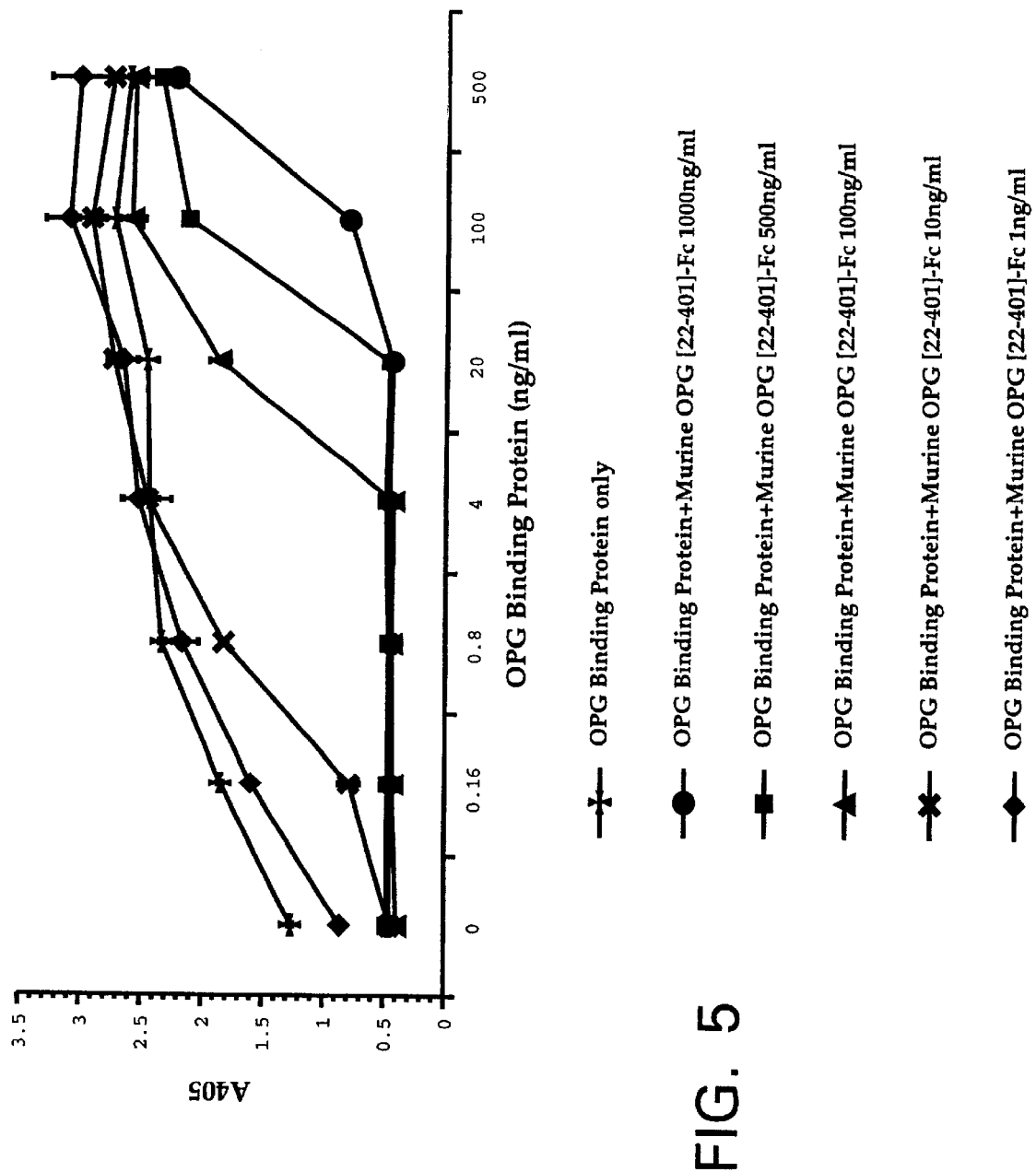
FIG. 5. Stimulation of osteoclast development in vitro from bone marrow macrophage and ST2 cell cocultures treated with recombinant murine OPG binding protein [158–316]. Cultures were treated with varying concentrations of murine OPG binding protein ranging from 1.6 to 500 ng/ml. After 8–10 days, cultures were lysed, and TRAP activity was measured by solution assay. In addition, some cultures were simultaneously treated with 1, 10, 100, 500, and 1000 ng/ml of recombinant murine OPG [22–401]-Fc protein. Murine OPG binding protein induces a dose-dependent stimulation in osteoclast formation, whereas OPG [22–401]-Fc inhibits osteoclast formation.
Figure 6:
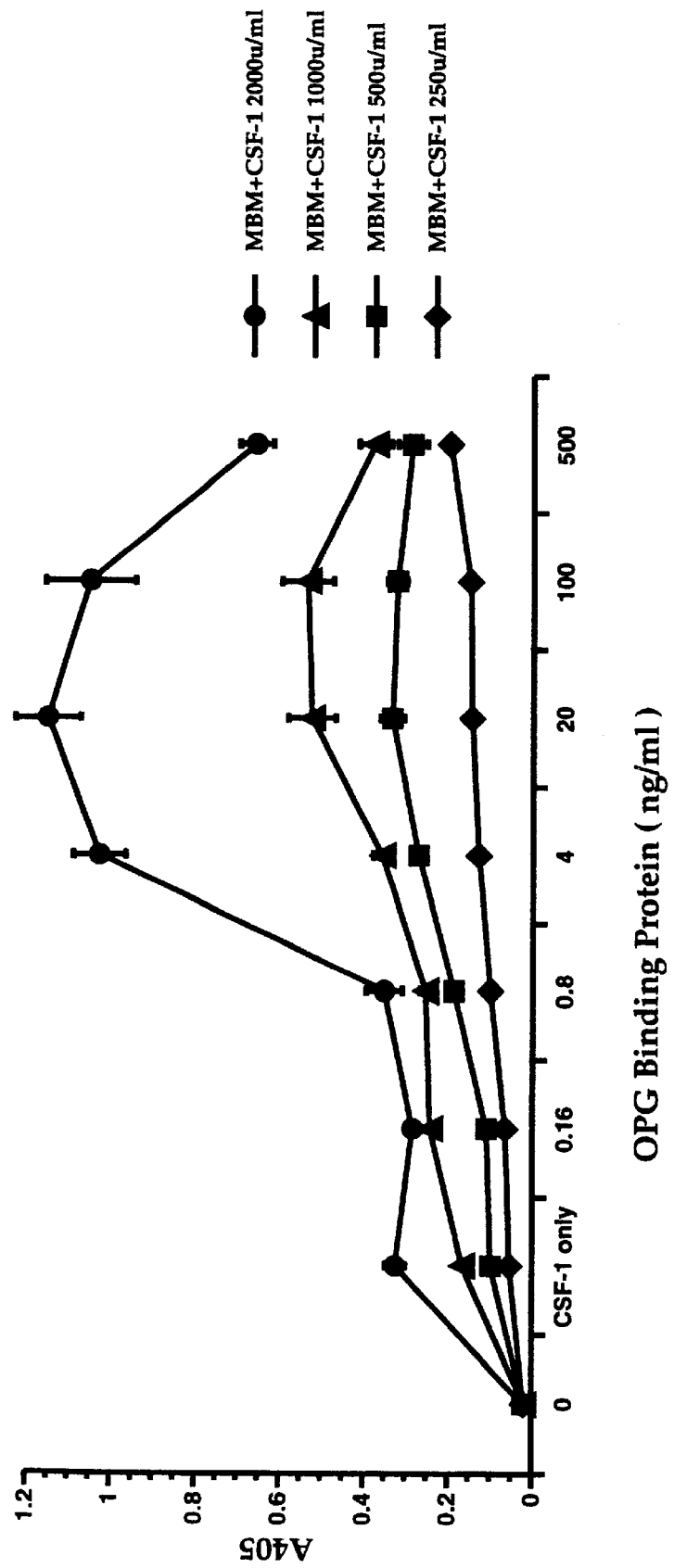
FIG. 6. Stimulation of osteoclast development from bone marrow precursors in vitro in the presence of M-CSF and murine OPG binding protein [158–316]. Mouse bone marrow was harvested, and cultured in the presence 250, 500, 1000, and 2000 U/ml of M-CSF. Varying concentrations of OPG binding protein [158–316], ranging from 1.6 to 500 ng/ml, were added to these same cultures. Osteoclast development was measured by TRAP solution assay.

Recombinant OPG protein has previously been shown to block vitamin D3-dependent osteoclast formation from bone marrow and spleen precursors in an osteoclast forming assay as described in U.S. Ser. No. 08/577,788. Since OPG binding protein binds to OPG, and is a novel member of the TNF family of ligands, it is a potential target of OPG bioactivity. Recombinant soluble OPG binding protein (158–316), representing the minimal core TNFα-like domain, was tested for its ability to modulate osteoclast differentiation from osteoclast precursors. Bone marrow cells were isolated from adult mouse femurs, and treated with M-CSF. The non-adherent fraction was co-cultured with ST2 cells in the presence and absence of both vitamin D3 and dexamethasone. As previously shown, osteoclasts develop only from co-cultures containing stromal cells (ST2), vitamin D3 and dexamethasone. Recombinant soluble OPG binding protein was added at varying concentrations ranging from 0.16 to 500 ng/ml and osteoclast maturation was determined by TRAP solution assay and by visual observation. OPG binding protein strongly stimulated osteoclast differentiation and maturation in a dose dependent manner, with half-maximal effects in the 1–2 ng/ml range, suggesting that it acts as an potent inducer of osteoclastogenesis in vitro (FIG. 5). The effect of OPG binding protein is blocked by recombinant OPG (FIG. 6).

To test whether OPG binding protein could replace the stroma and added steroids, cultures were established using M-CSF at varying concentrations to promote the growth of osteoclast precursors and various amounts of OPG binding protein were also added. As shown in FIG. 6, OPG binding protein dose dependently stimultated TRAP activity, and the magnitude of the stimulation was dependent on the level of added M-CSF suggesting that these two factors together are pivotal for osteoclast development. To confirm the biological relevance of this last observation, cultures were established on bovine cortical bone slices and the effects of M-CSF and OPG binding protein either alone or together were tested. As shown in FIG. 7, OPG binding protein in the presence of M-CSF stimulated the formation of large TRAP positive osteoclasts that eroded the bone surface resulting in pits. Thus, OPG binding protein acts as an osteoclastogenesis stimulating (differentiation) factor. This suggests that OPG blocks osteoclast development by sequestering OPG binding protein.

EXAMPLE 9

In vivo activity of recombinant soluble OPG Binding Protein

Based on in vitro studies, recombinant murine OPG binding protein [158–316] produced in E. coli is a potent inducer of osteoclast development from myeloid precursors. To determine its effects in vivo, male BDF1 mice aged 4–5 weeks (Charles River Laboratories) received subcutaneous injections of OPG binding protein [158–316] twice a day for three days and on the morning of the fourth day (days 0, 1, 2, and 3). Five groups of mice (n=4) received carrier alone, or 1, 5, 25 or 100 μg/ of of OPG binding protein [158–316] per day. An additional 5 groups of mice (n=4) received the above doses of carrier or of OPG binding protein [158–316] and in addition received human Fc-OPG [22-194] at 1 mg/Kg/day (approximately 20 μg/day) by single daily subcutaneous injection. Whole blood ionized calcium was determined prior to treatment on day 0 and 3–4 hours after the first daily injection of of OPG binding protein [158–316] on days 1, 2, and 3. Four hours after the last injection on day 3 the mice were sacrificed and radiographs were taken.

Figure 8:
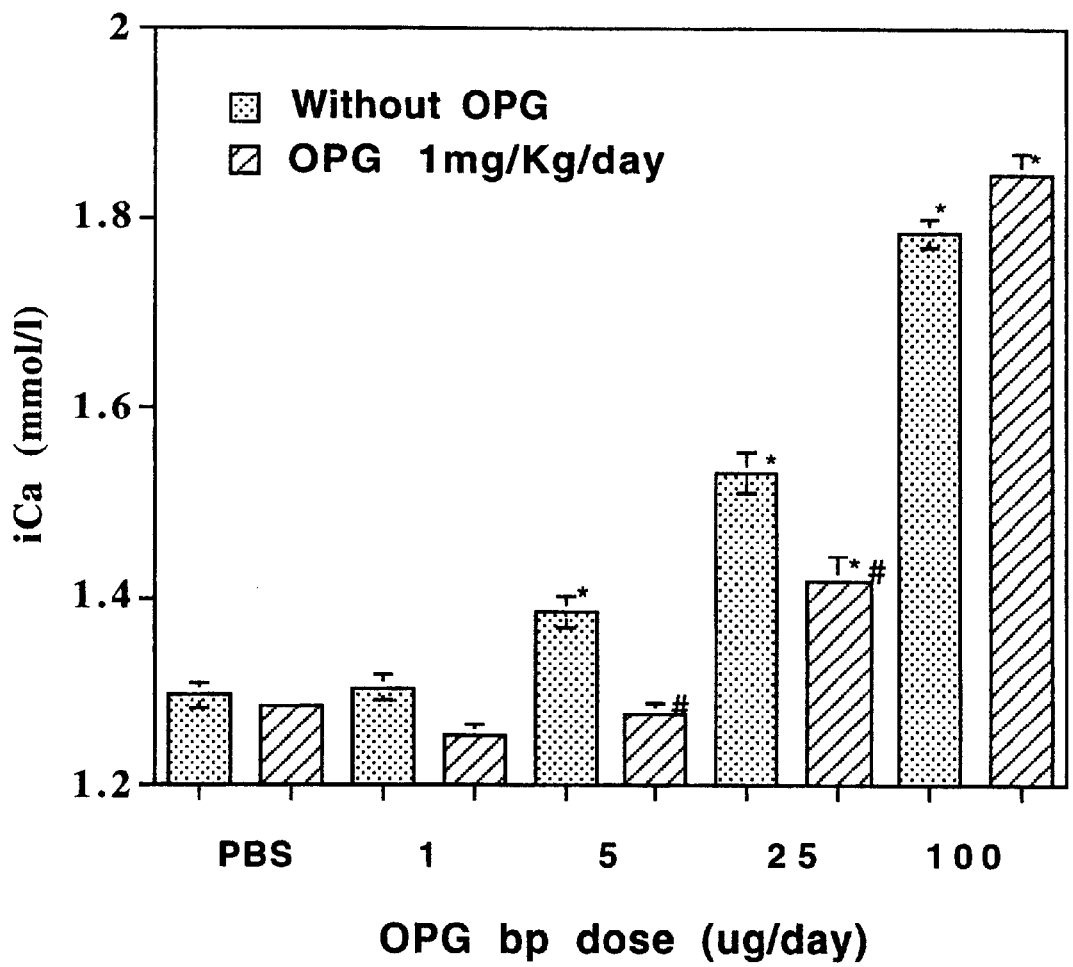
FIG. 8. Graph showing the whole blood ionized calcium (iCa) levels from mice injected with OPG binding protein, 51 hours after the first injection, and in mice also receiving concurrent OPG administration. OPG binding protein significantly and dose dependently increased iCa levels. OPG (1 mg/kg/day) completely blocked the increase in iCa at a dose of OPG binding protein of 5 ug/day, and partially blocked the increase at a dose of OPG binding protein of 25 ug/day. (*), different to vehicle treated control ($p<0.05$). (#), OPG treated iCa level significantly different to level in mice receiving that dose of OPG binding protein alone ($p<0.05$).
Figure 9A:
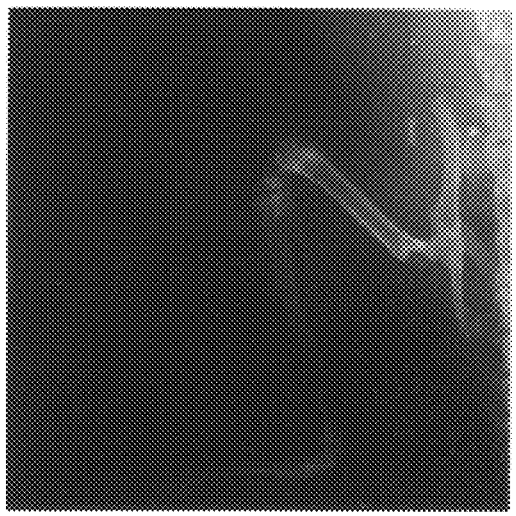
FIG. 9. Radiographs of the left femur and tibia in mice treated with 0, 5, 25 or 100 $\mu$g/day of OPG binding protein for 3.5 days. There is a dose dependent decrease in bone density evident most clearly in the proximal tibial metaphysis of these mice, and that is profound at a dose of 100 $\mu$g/day.
Figure 9B:
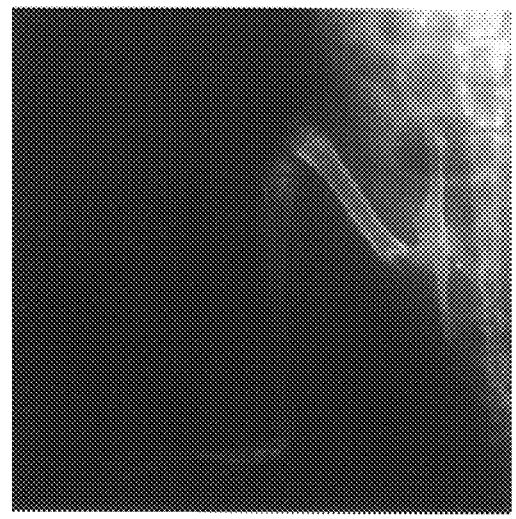
Figure 9C:
Figure 9D:
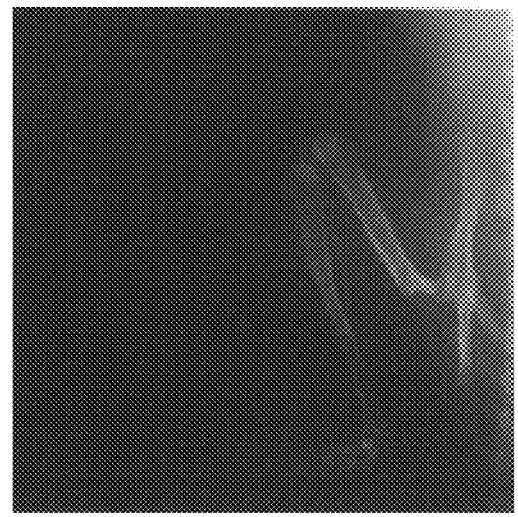

Recombinant of OPG binding protein [158–316] produced a significant increase in blood ionized calcium after two days of treament at dose of 5 μg/day and higher (FIG. 8). The severity of the hypercalcemia indicates a potent induction of osteoclast activity resulting from increased bone resorption. Concurrent OPG administration limited hypercalcemia at doses of OPG binding protein [158–316] of 5 and 25 μg/day, but not at 100 μg/day. These same animal were analysed by radiography to determine if there were any effects on bone mineral density visible by X-ray (FIG. 9). Recombinant of OPG binding protein [158–316] injected for 3 days decreased bone density in the proximal tibia of mice in a dose-dependent manner. The reduction in bone density was particularly evident in mice receiving 100 μg/d confirming that the profound hypercalcemia in these animals was produced from increased bone resorption and the resulting release of calcium from the skeleton. These data clearly indicate that of OPG binding protein [158–316] acts in vivo to promote bone resorption, leading to systemic hypercalcemia, and recombinant OPG abbrogates these effects.

EXAMPLE 10

Cloning and Expression of soluble OPG Binding Protein in mammalian cells

The full length clone of murine and human OPG binding protein can be expressed in mammalian cells as previously described in Example 2. Alternatively, the cDNA clones can be modified to encode secreted forms of the protein when expressed in mammalian cells. To do this, the natural 5' end of the cDNA encoding the intiation codon, and extending approximately through the first 69 amino acid of the protein, inluding the transmembrane spanning region, could be replaced with a signal peptide leader sequence. For example, DNA sequences encoding the initiation codon and signal peptide of a known gene can be spliced to the OPG binding protein cDNA sequence beginning anywhere after the region encoding amino acid residue 68. The resulting recombinant clones are predicted to produce secreted forms of OPB binding protein in mammalian cells, and should undergo post translational modifications which normally occur in the C-terminal extracellular domain of OPG binding protein, such as glycoslyation. Using this strategy, a secreted form of OPG binding protein was constructed which has at its 5' end the murine OPG signal peptide, and at its 3' end the human IgG1 Fc domain. The plasmid vector pCEP4/muOPG [22–401]-Fc as described in U.S. Ser. No. 08/577,788, filed Dec. 22, 1995, was digested with NotI to cleave between the 31 end of OPG and the Fc gene. The linearized DNA was then partially digested with XmnI to cleave only between residues 23 and 24 of OPG leaving a blunt end. The restriction digests were then dephosphorylated with CIP and the vector portion of this digest (including residues 1–23 of OPG and Fc) was gel purified.

The murine OPG binding protein cDNA region encoding amino acid reisudes 69–316 were PCR amplified using Pfu Polymerase (Stratagene, San Diego, Calif.) from the plasmid template using primers the following oligonucleotides:

1602-61: CCT CTA GGC CTG TAC TTT CGA GCG CAG ATG (SEQ ID NO: 27)

1602-59: CCT CTG CGG CCG CGT CTA TGT CCT GAA CTT TG (SEQ ID NO: 28)

The 1602-61 oligonucleotide amplifies the 5' end of the gene and contains an artificial an StuI site. The 1602-59 primer amplifies the 3' end of the gene and contians an artifical NotI site. The resulting PCR product obtained was digested with NotI and StuI, then gel purified. The purified PCR product was ligated with vector, then used to transform electrocompetent *E. coli* DH10B cells. The resulting clone was sequenced to confirm the intergrity of the amplified sequence and restriction site junctions. This plasmid was then used to transfect human 293 fibroblasts, and the OPG binding protein-Fc fusion protein was collected form culture media as previously described in U.S. Ser. No. 08/577,788, filed Dec. 22, 1995.

Using a similar strategy, an expression vector was designed that is capable of expressing a N-terminal truncation of fused to the human IgG1 Fc domain. This construct consists of the murine OPG signal peptide (aa residue 1–21), fused in frame to murine OPG binding protein residues 158–316, followed by an inframe fusion to human IgG1 Fc domain. To do this, the plasmid vector pCEP4/ murine OPG [22–401] (U.S. Ser. No. 08/577,788, filed Dec. 22, 1995), was digested with HindIII and NotI to remove the entire OPG reading frame. Murine OPG binding protein, residues 158–316 were PCR amplified using from the plasmid template pCDNA/32D-F3 using the following primers:

1616-44: CCT CTC TCG AGT GGA CAA CCC AGA AGC CTG AGG CCC AGC CAT TTG C (SEQ ID NO: 29)

1602-59: CCT CTG CGG CCG CGT CTA TGT CCT GAA CTT TG (SEQ ID NO: 30)

1616-44 amplifies OPG binding protein starting at residue 158 as well as containing residues 16–21 of the muOPG signal peptide with an artificial XhoI site. 1602-59 amplifies the 3' end of the gene and adds an in-frame NotI site. The PCR product was digested with NotI and XhoI and then gel purified.

The Follwing complimentary primers were annealed to eachother to form an adapter encoding the murine OPG signal peptide and Kozak sequence surrounding the translation initiation site:

1616-41: AGC TTC CAC CAT GAA CAA GTG GCT GTG CTG CGC ACT CCT GGT GCT CCT GGA CAT CA (SEQ ID NO: 31)

1616-42: TCG ATG ATG TCC AGG AGC ACC AGG AGT GCG CAG CAC AGC CAC TTG TTC ATG GTG GA (SEQ ID NO: 32)

These primers were annealed, generating 5' overhangs compatible with HindIII on the 5' end and XhoI on the 3' end. The digested vector obtianed above, the annealed oligos, and the digested PCR fragment were ligated together and electroporated into DH10B cells. The resulting clone was sequenced to confirm authentic reconstruction of the junction between the signal peptide, OPG binding protein fragment encoding residues 158–316, and the IgG1 Fc domain. The recombiant plasmid was purified, transfected into human 293 fibroblasts, and expressed as a conditioned media product as described above.

Full length murine and human cDNAs were cloned into the pCEP4 expression vector (Invitrogen, San Diego, Calif.) then transfected into cultures of human 293 fibroblasts as described in Example 1. The cell cultures were selected with hygromycin as described above and serum-free conditioned media was prepared. The conditioned media was exposed to a column of immobilized recombinant OPG, and shed forms of murine and human recombinant OPG bp were affinity purified. N-terminal sequence analysis of the purified soluble OPG binding proteins indicates that the murine protein is preferentially cleaved before phenylalanine 139, and the human protein is preferentially cleaved before the homologous residue, isoleucine 140. In addition the human protein is also preferentially cleaved before glycine 145. This suggests that naturally occurring soluble forms of human OPG binding protein have amino terminal residues at either isoleucine at position 140 or glycine at position 145.

EXAMPLE 11

Peptides of the OPG binding protein and preparation of polyclonal and monoclonal antibodies to the protein Antibodies to specific regions of the OPG binding protein may be obtained by immunization with peptides from OPG binding protein. These peptides may be used alone, or conjugated forms of the peptide may be used for immunization.

The crystal structure of mature TNFα has been described [E. Y. Jones, D. I. Stuart, and N. P. C. Walker (1990) J. Cell Sci. Suppl. 13, 11–18] and the monomer forms an antiparallel β-pleated sheet sandwich with a jellyroll topology. Ten antiparallel β-strands are observed in this crystal structure and form a beta sandwich with one beta sheet consisting of strands B'BIDG and the other of strands C'CHEF [E. Y. Jones et al., ibid.] Two loops of mature TNFα have been implicated from mutagenesis studies to make contacts with receptor, these being the loops formed between beta strand B & B' and the loop between beta strands E & F [C. R. Goh, C-S. Loh, and A. G. Porter (1991) Protein Engineering 4, 785–791]. The crystal structure of the complex formed between TNFβ and the extracellular domain of the 55 kd TNF receptor (TNF-R55) has been solved and the receptor-ligand contacts have been described [D. W. Banner, A. D'Arcy, W. Janes, R. Gentz, H-J. Schoenfeld, C. Broger, H. Loetscher, and W. Lesslauer (1993) Cell 73, 431–445]. In agreement with mutagenesis studies described above [C. R. Goh et al., ibid.] the corresponding loops BB' and EF of the ligand TNFβ were found to make the majority of contacts with the receptor in the resolved crystal structure of the TNFb:TNF-R55 complex. The amino acid sequence of murine OPG binding protein was compared to the amino acid sequences of TNFα and TNFβ. The regions of murine OPG binding protein corresponding to the BB' and EF loops were predicted based on this comparison and peptides have been designed and are described below A. Antigen(s): Recombinant murine OPG binding protein [158–316] has been used as an antigen (ag) for immunization of animals as described below, and serum will be examined using approaches described below. Peptides to the putative BB' and EF loops of murine OPG binding protein have been synthesized and will be used for immunization; these peptides are:

BB' loop peptide: NH2--NAASIPSGSHKVTLSSWYHDRGWAKIS-—COOH (SEQ ID NO: 33).

BB' loop-Cys peptide: NH2--NAASIPSGSHKVTLSSWYHDRGWAKISC—COOH (SEQ ID NO: 34)

EF loop peptide: NH2--VYVVKTSIKIPSSHNLM-—COOH (SEQ ID NO: 35)

EF loop-Cys peptide: NH2--VYVVKTSIKIPSSHNLMC-—COOH (SEQ ID NO: 36)

Peptides with a carboxy-terminal cysteine residue have been used for conjugation using approaches described in section B below, and have been used for immunization.

B. Keyhole Limpet Hemocyanin or Bovine Serum Albumin Conjugation: Selected peptides or protein fragments may be conjugated to keyhole limpet hemocyanin (KLH) in order to increase their immunogenicity in animals. Also, bovine serum albumin (BSA) conjugated peptides or protein fragments may be utilized in the EIA protocol. Imject Maleimide Activated KLH or BSA (Pierce Chemical Company, Rockford, Ill.) is reconstituted in $dH_2O$ to a final concentration of 10 mg/ml. Peptide or protein fragments are dissolved in phosphate buffer then mixed with an equivalent mass (g/g) of KLH or BSA. The conjugation is allowed to react for 2 hours at room temperature (rt) with gentle stirring. The solution is then passed over a desalting column or dialyzed against PBS overnight. The peptide conjugate is stored at −20° C. until used in immunizations or in EIAs.

C. Immunization: Balb/c mice, (Charles Rivers Laboratories, Wilmington, Mass.) Lou rats, or New Zealand White rabbits will be subcutaneously injected (SQI) with ag (50 μg, 150 μg, and 100 μg respectively) emulsified in Complete Freund's Adjuvant (CFA, 50% vol/vol; Difco Laboratories, Detroit, Mich.). Rabbits are then boosted two or three times at 2 week intervals with antigen prepared in similar fashion in Incomplete Freund's Adjuvant (ICFA; Difco Laboratories, Detroit, Mich.). Mice and rats are boosted approximately every 4 weeks. Seven days following the second boost, test bleeds are performed and serum antibody titers determined. When a titer has developed in rabbits, weekly production bleeds of 50 mls are taken for 6 consecutive weeks. Mice and rats are selected for hybridoma production based on serum titer levels; animals with half-maximal titers greater than 5000 are used. Adjustments to this protocol may be applied by one skilled in the art; for example, various types of immunomodulators are now available and may be incorporated into this protocol.

D. Enzyme-linked Immunosorbent Assay (EIA):

EIAs will be performed to determine serum antibody (ab) titres of individual animals, and later for the screening of potential hybridomas. Flat bottom, high-binding, 96-well microtitration EIA/RIA plates (Costar Corporation, Cambridge, Mass.) will be coated with purified recombinant protein or protein fragment (antigen, ag) at 5 μg per ml in carbonate-bicarbonate buffer, pH 9.2 (0.015 M $Na_2CO_3$, 0.035M $NaHCO_3$). Protein fragments may be conjugated to bovine serum albumin (BSA) if necessary. Fifty μl of ag will be added to each well. Plates will then be covered with acetate film (ICN Biomedicals, Inc., Costa Mesa, Calif.) and incubated at room temperature (rt) on a rocking platform for 2 hours or over-night at 4° C. Plates will be blocked for 30 minutes at rt with 250 μl per well 5% BSA solution prepared by mixing 1 part BSA diluent/blocking solution concentrate (Kirkegaard and Perry Laboratories, Inc., Gaithersburg, Md.) with 1 part deionized water ($dH_2O$). Blocking solution having been discarded, 50 μl of serum 2-fold dilutions (1:100 through 1: 12,800) or hybridoma tissue culture supernatants will be added to each well. Serum diluent is 1% BSA (10% BSA diluent/blocking solution concentrate diluted 1:10 in Dulbecco's Phosphate Buffered Saline, D-PBS; Gibco BRL, Grand Island, N.Y.)) while hybridoma supernatants are tested undiluted. In the case of hybridoma screening, one well is maintained as a conjugate control, and a second well as a positive ab control. Plates are again incubated at rt, rocking for 1 hour, then washed 4 times using a 1 x preparation of wash solution 20 x concentrate (Kirkegaard and Perry Laboratories, Inc., Gaithersburg, Md.) in $dH_2O$. Horseradish peroxidase conjugated secondary ab (Boeringer Mannheim Biochemicals, Indianapolis, Ind.) diluted in 1% BSA is then incubated in each well for 30 minutes. Plates are washed as before, blotted dry, and ABTS peroxidase single component substrate (Kirkegaard and Perry Laboratories, Inc., Gaithersburg, Md.) is added. Absorbance is read at 405 nm for each well using a Microplate EL310 reader (Bio-tek Instruments, Inc., Winooski, Vt.). Half-maximal titre of serum antibody is calculated by plotting the $\log_{10}$ of the serum dilution versus the optical density at 405, then extrapolating at the 50% point of the maximal optical density obtained by that serum. Hybridomas are selected as positive if optical density scores greater than 5-fold above background. Adjustments to this protocol may be applied; in example, conjugated secondary antibody may be chosen for specificity or non-cross-reactivity.

E. Cell fusion: The animal selected for hybridoma production is intravenously injected with 50 to 100 μg of ag in PBS. Four days later, the animal is sacrificed by carbon dioxide and its spleen collected under sterile conditions into 35 ml Dulbeccos' Modified Eagle's Medium containing 200 U/ml Penicillin G, 200 μg/ml Streptomycin Sulfate, and 4 mM glutamine (2 x P/S/G DMEM). The spleen is trimmed of excess fatty tissue, then rinsed through 4 dishes of clean 2 x P/S/G DMEM. It is next transferred to a sterile stomacher bag (Tekmar, Cincinnati, Ohio) containing 10 ml of 2 x P/S/G DMEM and disrupted to single cell suspension with the Stomacher Lab Blender 80 (Seward Laboratory UAC House; London, England). As cells are released from the spleen capsule into the media, they are removed from the bag and transferred to a sterile 50 ml conical centrifuge tube (Becton Dickinson and Company, Lincoln Park, N.J.). Fresh media is added to the bag and the process is continued until the entire cell content of the spleen is released. These splenocytes are washed 3 times by centrifugation at 225 x g for 10 minutes.

Concurrently, log phase cultures of myeloma cells, Sp2/0-Ag14 or Y3-Ag1.2.3 for mouse or rat splenocyte fusions, respectively, (American Type Culture Collection; Rockville, Md.) grown in complete medium (DMEM, 10% inactivated fetal bovine serum, 2 mm glutamine, 0.1 mM non-essential amino acids, 1 mM sodium pyruvate, and 10 mM hepes buffer; Gibco Laboratories, Grand Island, N.Y.) are washed in similar fashion. The splenocytes are combined with the myeloma cells and pelleted once again. The media is aspirated from the cell pellet and 2 ml of polyethylene glycol 1500 (PEG 1500; Boehringer Mannheim Biochemicals, Indianapolis, Ind.) is gently mixed into the cells over the course of 1 minute. Thereafter, an equal volume of 2 x P/S/G DMEM is slowly added. The cells are allowed to fuse at 37° C. for 2 minutes, then an additional 6 ml of 2 x P/S/G DMEM is added. The cells are again set at 37° C. for 3 minutes. Finally, 35 ml of 2 x P/S/G DMEM is added to the cell suspension, and the cells pelleted by centrifugation. Media is aspirated from the pellet and the cells gently resuspended in complete medium. The cells are distributed over 96-well flat-bottom tissue culture plates (Becton Dickinson Labware; Lincoln Park, N.J.) by single drops from a 5 ml pipette. Plates are incubated overnight in humidified conditions at 37° C. 5% $CO_2$. The next day, an equal volume of selection medium is added to each well. Selection consists of 0.1 mM hypoxanthine, $4 \times 10^{-4}$ mM aminopterin, and $1.6 \times 10^{-2}$ mM thymidine in complete medium. The fusion plates are incubated for 7 days followed by 2 changes of medium during the next 3 days; HAT selection medium is used after each fluid change. Tissue culture supernatants are taken 3 to 4 days after the last fluid change from each hybrid-containing well and tested by EIA for specific antibody reactivity. This protocol has been modified by that in Hudson and Hay, "Practical Immunology, Second Edition", Blackwell Scientific Publications.

EXAMPLE 12

Cloning of an OPG Binding Protein Receptor Expressed on Hematopoietic Precursor cells Biologically active recombinant murine OPG binding protein [158–316] was conjugated to fluorescein-isothyocyanate (FITC) to generate a fluorescent probe. Fluorescent labeling was performed by incubation of recombinant murine OPG binding protein [158–316] with 6-fluorescein-5-(and 6) carboxyamido hexanoic acid succinimidyl ester (Molecular Probes, Eugene, Oreg.) at a 1:6 molar ratio for 12 hrs. at 4° C. FITC-labeled OPG binding protein [158–316] was further purified by gel filtration chromatography. Mouse bone marrow cells were isolated and incubated in culture in the presence of CSF-1 and OPG binding protein [158–316] as described in Example 10. Mouse bone marrow cells were cultured overnight in CSF-1 (30 ng/ml) and OPG binding protein [158–316] (20 ng/ml). Non-adherent cells were removed first and stored on ice and the remaining adherent cells were removed by incubating with cell dissociation buffer (Sigma Chemicals, St. Louis, Mo.), pooled with the non-adherent population, and then stained with FITC-OPG binding protein as described above. After washing and resuspending in PBS with 0.5% BSA, the cells were exposed to FITC-OPG binding protein, washed, then sorted by FACS. The population of cells that were postive for staining with the FITC-OPG binding protein was collected and mRNA was isolated as described in Example 2. This mRNA preparation was used to make a cDNA library following procedures described in Example 2.

The cDNA library produced from this source was used for random EST sequence analysis as previously described in PCT Publication No. WO97/23614 and in Simonet et al. (Cell 89, 309–319 (1997)). Using this method, an ~2.1 kb cDNA was detected that encoded a novel TNFR-related protein. The long open reading frame of the murine ODAR cDNA encodes a protein of 625 amino acid residues and contains the hallmark features of TNFR-related proteins: a hydrophobic signal peptide at its N-termini, four tandem cysteine-rich repeat sequences, a hydrophobic transmembrane domain, and a cytoplasmic signalling domain. The homology of this protein with other members of the TNF receptor family and its expression in bone marrow cells that bind FITC-labelled OPG binding protein suggest that it is a potential receptor for the TNF-related OPG binding protein. This protein is designated ODAR, or osteoclast differentiation and activation receptor. The nucleic acid sequence and predicted amino acid sequence of murine ODAR is shown in FIG. 10.

Recent analysis of sequences in publicly available databases indicate that this protein is the murine homolog of a human TNFR-related protein known as RANK (Anderson et al., Nature 390, 175–179 (1997)).

EXAMPLE 13

Production of Recombinant ODAR Protein in Mammalian Cells

A soluble ODAR extracellular domain fused to the Fc region of human $IgG_1$ was produced using procedures for the construction and expression of Fc fusion proteins as previously described in WO97/23614 and in Simonet et al., supra. To generate soluble ODAR protein in mammalian cells, cDNA encoding extracellular domain of murine ODAR (amino acids 27–211) was PCR amplified with the following set of oligonucleotide primers:

5' TCT CCA AGC TTG TGA CTC TCC AGG TCA CTC C-3' (SEQ ID NO: 37)

5' TCT CCG CGG CCG CGT AAG CCT GGG CCT CAT TGG GTG-3' (SEQ ID NO: 38)

PCR reactions were carried in a volume of 50 ∥l with 1 unit of vent DNA polymerase (New England Biolabs) in 20 mM Tris-HCl pH 8.8, 10 mM KCl, 10 mM $(NH_4)_2SO_4$, 0.1% Triton-X100, 10 $\mu M$ of each dNTP, 1 $\mu M$ of each primer and 10 ng of ODAR cDNA template. Reactions were performed in 94° C. for 30 s, 55° C. for 30 s, and 72° C. for 1 min, for a total of 16 cycles. The PCR fragment was isolated by electrophoresis. The PCR fragment creates a Hind III restriction site at 5' end and a Not I restriction site at 3' end. The Hind III-Not I digested PCR fragment was then subcloned in-frame into a modified pCEP4-Fc vector in front of the human IgG-γ1 heavy chain sequence as described previously in WO97/23614 and in Simonet et al. supra). A linker was introduced which encodes two irrelevant amino acids spanning the junction between the ODAR extracellular domain and the IgG Fc region.

The construct was then digested with Nhe I and Hind III and the following annealed oligonucleotide pair encoding OPG signal peptide (amino acid 1–21) was inserted in-frame:

5' CTA GCA CCA TGA ACA AGT GGC TGT GCT GCG CAC TCC TGG TGC TCC TGG ACA TCA TTG AAT GGA CAA CCC AGA-3' (SEQ ID NO: 39)

5'AGC TTC TGG GTT GTC CAT TCA ATG ATG TCC AGG AGC ACC AGG AGT GCG CAG CAC AGC CAC TTG TTC ATG GTG-3' (SEQ ID NO: 40)

A linker which encodes two irrelevant amino acids was introduced between OPG signal peptide and ODAR sequences. The final engineered construct (ODAR-Fc/pCEP4) encodes a fusion protein containing from amino terminus to carboxy terminus: OPG signal peptide (amino acids 1–21)-linker (LysLeu)-ODAR (amino acids 27–211)-linker (AlaAla)-human IgG Fc.

The construct was transfected into 293-EBNA-1 cells by calcium phosphate method as described (Ausubel et al., Curr. Prot. Mol. Biol. 1, 9.1.1–9.1.3, (1994). The transfected cells were then selected in 200 $\mu g/ml$ hygromycin (GibcoBRL) and the resulting drug-resistant mass cultures were pooled and grown to confluence. The cells were washed in PBS once and then cultured in serum-free media for 72 hr. The conditioned media was collected. The ODAR-Fc fusion protein in the media was detected by western blot analysis with anti-human IgG Fc antibody.

The Fc fusion protein was purified by protein-A column chromatography (Pierce) using the manufacturer's recommended procedures. Fifty pmoles of the purified protein was then subjected to N-terminal sequence analysis by automated Edman degradation as essentially described by Matsudaira et al (J. Biol. Chem. 262, 10–35 (1987)). The following amino acid sequence was read after 10 cycles:

$NH_2$- K L V T L Q V T P-$CO_2H$41.

Figure 11A:
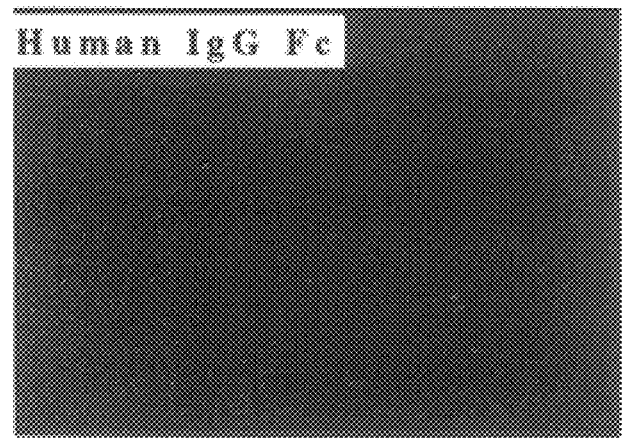
FIG. 11. Immunofluorescent staining of ODAR-Fc binding to OPG binding protein transfected cells. COS-7 cells transfected with OPG binding protein expression plasmid were incubated with human IgG Fc (top panel), ODAR-Fc (middle panel) or OPG-Fc (bottom panel). A FITC-labeled goat anti-human IgG Fc antibody was used as a secondary antibody. Positive binding cells were examined by confocal microscopy.
Figure 11B:
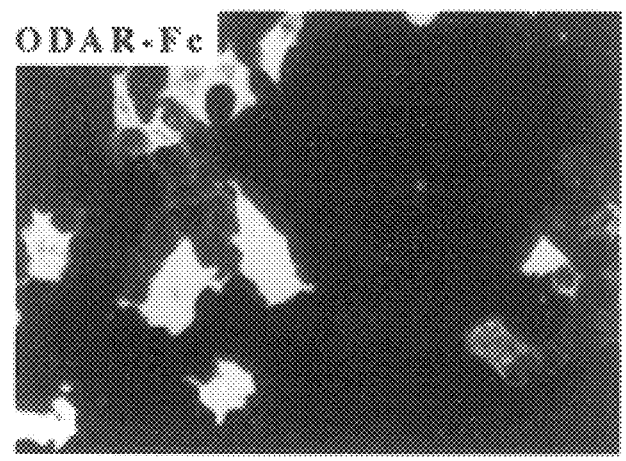
Figure 11C:
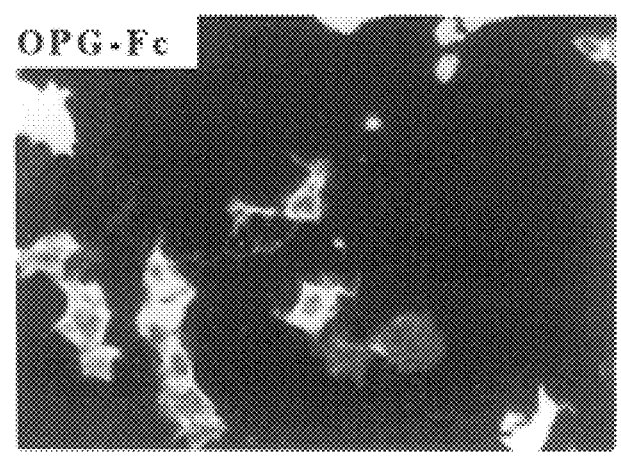
Figure 12A:
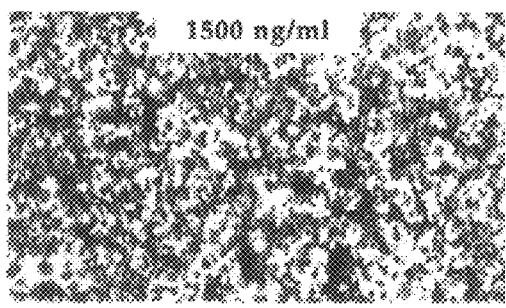
FIG. 12 . Effects of ODAR-Fc on the generation of osteoclasts from mouse bone marrow in vitro. Murine bone marrow cultures were established as in Example 8 and exposed to OPG binding protein (5 ng/ml) and CSF-1 (30 ng/ml). Various concentrations of ODAR-Fc ranging from 1500 ng/ml to 65 ng/ml were added. Osteoclast formation was assessed by TRAP cytochemistry and the TRAP solution assay after 5 days in culture.
Figure 12B:
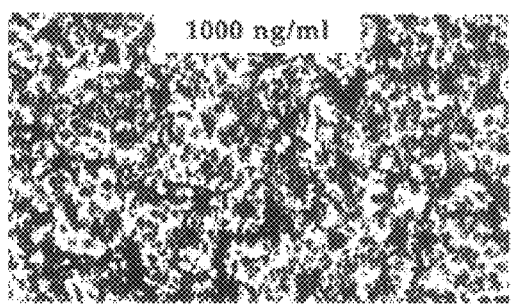
Figure 12C:
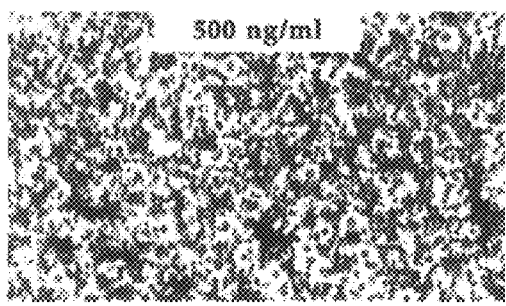
Figure 12D:
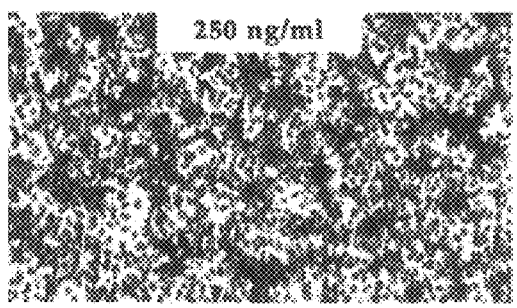
Figure 12E:
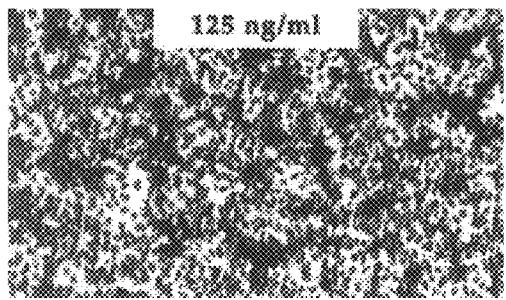
Figure 12F:
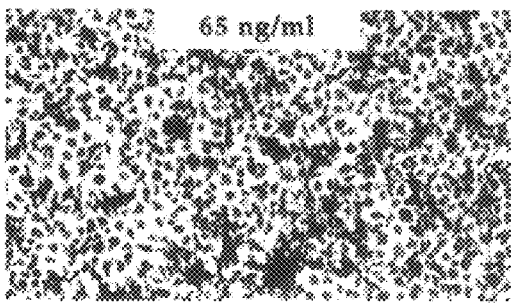
Figure 12G:
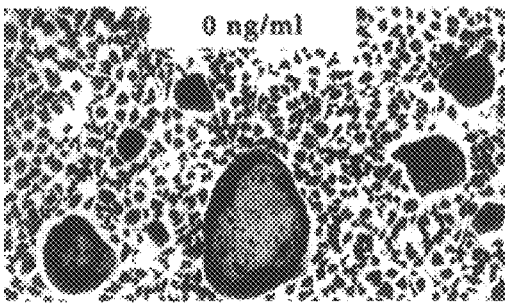
Figure 12H:
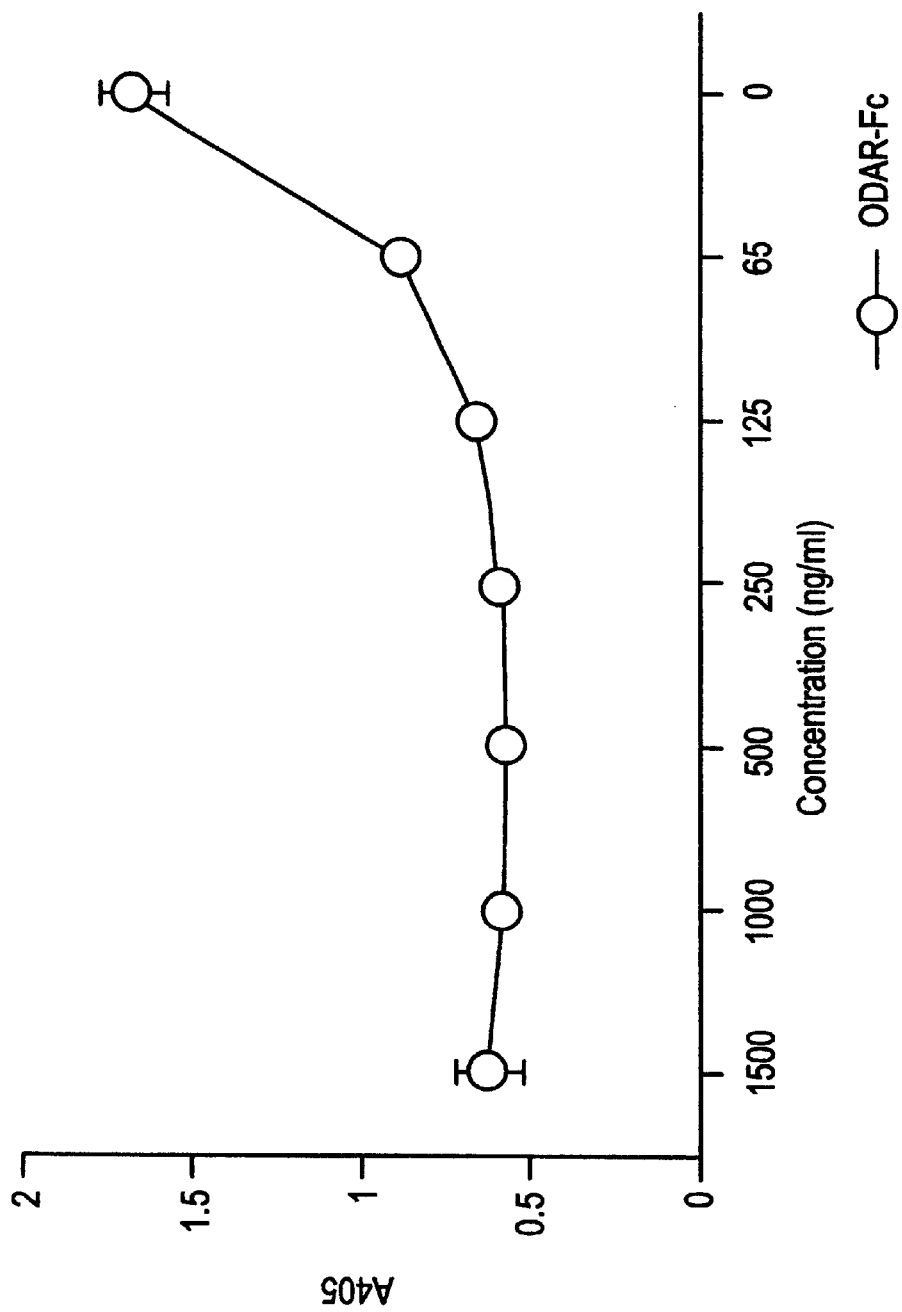

The binding activity of ODAR-Fc with OPG binding protein was examined by immunofluorescent staining of transfected COS-7 cell cultures as described in Example 2. COS-7 cells were lipofected with 1 μg of an expression vector containing DNA encoding murine OPG binding protein. After 48 hr incubation, cells were then incubated in PBS-FBS solution containing 10 mg/μl of human IgG Fc, ODAR-Fc, or OPG-Fc protein at 4° C. for 1 hr. Cells were then washed with PBS twice and then incubated in PBS-FBS solution containing 20 μg/ml FITC-labeled goat anti-human IgG (Southern Biotech Associates) for another hr. After washing with PBS, cells were examined by confocal microscopy (ACAS, Ultima, Insight Biomedical Imaging, Inc., Okemos, Mich.). Both ODAR-Fc and OPG-Fc bind to OPGL transfected COS-7 cells (FIG. 11).

EXAMPLE 14

In vitro biological activity of recombinant soluble ODAR

The ability of ODAR to inhibit stimulation of osteoclast formation by OPG binding protein was assessed in a mouse bone marrow culture in the presence of CSF-1 (30 ng/ml) and OPG binding protein (5 ng/ml). Procedures for the use of mouse bone marrow cultures to study osteoclast maturation are described in WO97/23614 and in Example 8. ODAR-Fc fusion protein produced as described in Example 12 was added to concentrations of 65 to 1500 ng/ml. Osteoclast formation was assessed by tartrate resistant alkaline phosphotase (TRAP) cytochemistry and the TRAP solution assay after five days in culture.

A dose dependent inhibition of osteoclast formation by ODAR-Fc fusion was observed both by cytochemistry and by TRAP activity (FIG. 12). ODAR-Fc fusion protein inhibited osteoclast formation with an $ED_{50}$ of about 10–50 ng/ml.

EXAMPLE 15

In vivo biological activity of recombinant soluble ODAR

Young rapidly growing male BDF1 mice aged 3–4 weeks received varying doses of ODAR-Fc fusion protein by single daily subcutaneous injection in carrier (PBS/0.1% BSA) for four days. The mice were x-rayed on day 5. Doses of ODAR-Fc fusion protein used were 0.5, 1.5 and 5 mg/kg/day. For each treatment, all the mice in that group and in the control group that received PBS/0.1% BSA were x-rayed on a single film. The proximal tibial metaphyseal region was compared between pairs of control and treated tibias and scored as a "+" if the treated tibia was denser by visual assessment than the control giving the 8 scores shown below. An arbitrary score of ⅝ was required for a "positive" result. (Dose is in mg/Kg/day). (n=4).

After sacrifice the the right tibia was removed from each animal and the bone density in the proximal tibial metaphysis was measured by peripheral quantitative computerized tomography (pQCT) (Stratec, Germany). Two 0.5 mm cross-sections of bone, 1.5 mm and 2.0 mm from the proximal end of the tibia were analyzed (XMICE 5.2, Stratec, Germany) to determine total bone mineral density in the metaphysis. A soft tissue separation threshold of 1500 was used to define the boundary of the metaphyseal bone.

ODAR-Fc administration in young growing mice inhibited bone resorption at the proximal tibial growth plate producing a region of increased bone density that was evident visually on radiographs. Radiographic changes were apparent at a dose of 1.5 mg/kg/day and above in two experiments (Table 1). Measurement of the bone density by pQCT in samples from the second experiment in a similar region of the tibia confirmed the dose dependent increased in bone density in these mice (FIG. 13).

TABLE 1

| Inhibition of bone resorption by ODAR-Fc fusion protein | | | | | | | | | | |
|---|---|---|---|---|---|---|---|---|---|---|
| Factor | Dose | 1 | 2 | 3 | 4 | 5 | 6 | 7 | 8 | Result |
| Experiment 1 | | | | | | | | | | |
| ODAR-Fc | 5.0 | + | + | + | + | + | + | + | + | Positive 8/8 |
| ODAR-Fc | 1.5 | − | + | + | − | + | + | + | + | Positive 6/8 |
| ODAR-Fc | 0.5 | − | − | − | − | − | − | − | − | Negative 0/8 |
| ODAR-Fc | 0.15 | − | − | − | − | − | − | − | − | Negative 0/8 |
| Experiment 2 | | | | | | | | | | |
| ODAR-Fc | 5.0 | + | + | + | + | + | + | + | + | Positive 8/8 |
| ODAR-Fc | 1.5 | + | + | + | + | + | + | + | + | Positive 8/8 |
| ODAR-Fc | 0.5 | − | − | − | + | − | − | − | − | Negative 1/8 |

\* \* \*

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method for preventing or treating bone disease in a mammal comprising administering to a mammal having reduced bone density or susceptible to reduced bone density a therapeutically effective amount of a soluble form of an osteoclast differentiation and activation receptor (ODAR).

2. The method of claim 1 wherein ODAR comprises a soluble form of human ODAR.

3. The method of claim 2 wherein the soluble form of human ODAR is lacking a functional transmembrane region.

4. The method of claim 2 wherein ODAR comprises part or all of the extracellular domain of human ODAR and is capable of binding to OPG binding protein.

5. The method of claim 2 wherein the soluble form of human ODAR is fused to a heterologous amino acid sequence.

6. The method of claim 5 wherein the heterologous amino acid sequence comprises an Fc region of human IgG.

7. The method of claim 1 wherein the mammal is a human.

8. The method of claim 1 wherein the bone disease is selected from the group consisting of osteoporosis, osteomyelitis, hypercalcemia of malignancy, osteopenia brought on by surgery or steroid administration, Paget's disease, osteonecrosis, bone loss due to rheumatoid arthritis, periodontal bone loss, immobilization, prosthetic loosening and osteolytic metastasis.

9. The method of claim 1 further comprising administering a therapeutically effective amount of a bone morphogenic factor, TGF-β family member, fibroblast growth factor, IL-1 inhibitor, TNF-α inhibitor, parathyroid hormone, E series prostaglandin, bisphoshponate, estrogen, SERM, or bone-enhancing mineral.

* * * * *

UNITED STATES PATENT AND TRADEMARK OFFICE
CERTIFICATE OF CORRECTION

PATENT NO. : 6,316,408 B1
DATED : November 13, 2001
INVENTOR(S) : William J. Boyle It is certified that error appears in the above-identified patent and that said Letters Patent is hereby corrected as shown below:

Title page,
Insert -- WO 86/00922  2/1986  (WO) --
Insert -- WO 93/12227  6/1993  (WO) --
Insert -- WO 96/26271  8/1996  (WO) --
Insert -- WO 97/23614  7/1997  (WO) --
Insert -- WO 98/28426  7/1998  (WO) --
Insert -- WO 98/25958  6/1998  (WO) --
Insert -- Anderson et al., "A homologue of the TNF receptor and its ligand enhance T-cell growth and dendritic-cell function", Nature, vol. 390, 1997, pp. 175-179. --
Insert -- Ausubel et al., Current Protocols in Molecular Biology, 18, 1995. --
Insert -- Banner et al., "Crystal Structure of the Soluble Human 55 kd TNF Receptor-Human TNFB Complex: Implications for TNF Receptor Activation", Cell, vol. 73, 1993, pp. 431-445. --
Insert -- Chomczynski et al., "Single-Step Method of RNA Isolation by Acid Guanidinium Thiocyanate-Phenol-Chloroform Extraction", Analytical Biochemistry, vol. 162, 1987, pp. 156-159. --
Insert -- Gennaro, Remington's Pharmaceutical Sciences, 18$^{th}$ Edition, 1980. --
Insert -- Goeddel, Methods in Enzymology, vol. 185, 1990. --
Insert -- Gribskov et al., "Profile analysis: Detection of distantly related proteins", Proc. Natl. Acad. Sci. USA, vol. 84, 1987, pp. 4355-4358. --
Insert -- Jimi et al., "Osteoclast Function is Activated by Osteoblastic Cells Through a Mechanism Involving Cell-to-Cell Contact", Endocrinology, vol. 137, No. 5, 1996, pp. 2187-2190. --
Insert -- Lüthy et al., "Improving the sensitivity of the sequence profile method", Protein Science, vol. 3, 1994, pp. 139-146. --
Insert -- Matsudaira, "Sequence from Picomole Quantities of Proteins Electroblotted onto Polyvinylidene Difluoride Membranes*", The Journal of Biological Chemistry, vol. 262, No. 21, 1987, pp. 10035-10038. --
Insert -- Montgomery et al., "Herpes Simplex Virus-1 Entry into Cells Mediated by a Novel Member of the TNF/NGF Receptor Family", Cell, vol. 87, 1996, pp. 427-436. --
Insert -- Nagata et al., "The Fas Death Factor", Science, vol. 267, 1995, pp. 1449-1456. --
Insert -- Pearson, "Rapid and Sensitive Sequence Comparison with FASTP and FASTA", Methods in Enzymology, vol. 183, 1990, pp. 63-98. --
Insert -- Sambrook et al., Molecular Cloning: A Laboratory Manual, Second Edition, 1989. --
Insert -- Simonet et al., "Osteoprotegerin: A Novel Secreted Protein Involved in the Regulation of Bone Density", Cell, vol. 89, 1997, pp. 309-319. --
Insert -- Smith et al., "The TNF Receptor Superfamily of Cellular and Viral Proteins: Activation, Costimulation, and Death", Cell, vol. 76, 1994, pp. 959-962. --

UNITED STATES PATENT AND TRADEMARK OFFICE
CERTIFICATE OF CORRECTION

PATENT NO. : 6,316,408 B1
DATED : November 13, 2001
INVENTOR(S) : William J. Boyle Page 2 of 4

It is certified that error appears in the above-identified patent and that said Letters Patent is hereby corrected as shown below:

Title page (cont.),
Insert -- Wiley et al., "Identification and Characterization of a New Member of the TNF Family that Induces Apoptosis", Immunity, vol. 3, 1995, pp. 673-682. --
Insert -- Yasuda et al., "Osteoclast differentiation factor is a ligand for osteoprotegerin/ osteoclastogenesis-inhibitory factor and is indentical to TRANCE/RANKL", Proc. Natl. Acad. Sci. USA, vol. 95, 1998, pp. 3597-3602. --
Insert -- E.M.B.L. Databases Accession Number AA170348, 1997. --

Item [57], line 2, change "osteolcast" to -- osteoclast --.

Column 2,
Line 35, change "doman" to -- domain --.
Line 66, change "marine" to -- murine --.

Column 3,
Line 20, change "releated" to -- related --.
Line 30, change "(SEQ ID NOS: 3 and 3)" to -- (SEQ ID NOS: 3 and 4) --.
Line 33, change "charbohydrate" to -- carbohydrate --.

Column 5,
Line 8, add -- to -- after "predicted".
Line 9, change "cytoplamsic" to -- cytoplasmic --.

Column 8,
Line 4, change "mamalian" to -- mammalian --.

Column 9,
Line 3, change "modificaitons" to -- modifications --.

Column 13,
Line 61, change "Biacre" to -- Biacore --.

Column 14,
Line 4, delete "of the" after "of the"
Line 54, change "anatagonists" to -- antagonists --.

Column 15,
Line 11, change "Anatoginists" to -- Antagonists --.

UNITED STATES PATENT AND TRADEMARK OFFICE
CERTIFICATE OF CORRECTION

PATENT NO. : 6,316,408 B1
DATED : November 13, 2001
INVENTOR(S) : William J. Boyle It is certified that error appears in the above-identified patent and that said Letters Patent is hereby corrected as shown below:

Column 16,
Line 65, change "polyliker" to -- polylinker --

Column 17,
Line 56, change "yeilding" to -- yielding --.

Column 18,
Lines 13 and 15, change "Univeristy" to -- University --.

Column 19,
Line 23, change "hybridiziation" to -- hybridization --.
Line 64, change "homologus" to -- homologous --.

Column 22,
Line 55, change "her" to -- here --.

Column 24,
Lines 28 and 34, delete "of" after "of".
Line 44, change "radiaography" to -- radiography --.
Line 67, change "inluding" to -- including --.

Column 25,
Line 6, change "OPB" to -- OPG --.
Line 22, change "reisudes" to -- residues --.
Line 31, change "contians" to -- contains --.
Line 64, change "Follwing" to -- following --.

Column 26,
Line 9, change "obtianed" to -- obtained --.

Column 30,
Line 29, change "111" to -- $\mu l$ --.

UNITED STATES PATENT AND TRADEMARK OFFICE
CERTIFICATE OF CORRECTION

PATENT NO. : 6,316,408 B1
DATED : November 13, 2001
INVENTOR(S) : William J. Boyle It is certified that error appears in the above-identified patent and that said Letters Patent is hereby corrected as shown below:

Column 32,
Line 12, delete "the" after "the".

Column 56,
Line 36, change "bisphoshponate" to -- bisphosphonate --.

Signed and Sealed this

Thirtieth Day of April, 2002

Attest:

Attesting Officer

JAMES E. ROGAN
*Director of the United States Patent and Trademark Office*

SEQUENCE LISTING

<160> NUMBER OF SEQ ID NOS: 40

<210> SEQ ID NO 1
<211> LENGTH: 2295
<212> TYPE: DNA
<213> ORGANISM: Mouse
<220> FEATURE:

-continued

```
<221> NAME/KEY: CDS
<222> LOCATION: (158)..(1105)

<400> SEQUENCE: 1
gagctcggat ccactactcg acccacgcgt ccggccagga cctctgtgaa ccggtcgggg     60
cgggggccgc ctggccggga gtctgctcgg cggtgggtgg ccgaggaagg gagagaacga    120
tcgcggagca gggcgcccga actccgggcg ccgcgcc atg cgc cgg gcc agc cga    175
                                          Met Arg Arg Ala Ser Arg
                                            1               5 gac tac ggc aag tac ctg cgc agc tcg gag gag atg ggc agc ggc ccc     223
Asp Tyr Gly Lys Tyr Leu Arg Ser Ser Glu Glu Met Gly Ser Gly Pro
         10                  15                  20 ggc gtc cca cac gag ggt ccg ctg cac ccc gcg cct tct gca ccg gct     271
Gly Val Pro His Glu Gly Pro Leu His Pro Ala Pro Ser Ala Pro Ala
     25                  30                  35 ccg gcg ccg cca ccc gcc gcc tcc cgc tcc atg ttc ctg gcc ctc ctg     319
Pro Ala Pro Pro Pro Ala Ala Ser Arg Ser Met Phe Leu Ala Leu Leu
 40                  45                  50 ggg ctg gga ctg ggc cag gtg gtc tgc agc atc gct ctg ttc ctg tac     367
Gly Leu Gly Leu Gly Gln Val Val Cys Ser Ile Ala Leu Phe Leu Tyr
 55                  60                  65                  70 ttt cga gcg cag atg gat cct aac aga ata tca gaa gac agc act cac     415
Phe Arg Ala Gln Met Asp Pro Asn Arg Ile Ser Glu Asp Ser Thr His
                 75                  80                  85 tgc ttt tat aga atc ctg aga ctc cat gaa aac gca ggt ttg cag gac     463
Cys Phe Tyr Arg Ile Leu Arg Leu His Glu Asn Ala Gly Leu Gln Asp
             90                  95                 100 tcg act ctg gag agt gaa gac aca cta cct gac tcc tgc agg agg atg     511
Ser Thr Leu Glu Ser Glu Asp Thr Leu Pro Asp Ser Cys Arg Arg Met
        105                 110                 115 aaa caa gcc ttt cag ggg gcc gtg cag aag gaa ctg caa cac att gtg     559
Lys Gln Ala Phe Gln Gly Ala Val Gln Lys Glu Leu Gln His Ile Val
    120                 125                 130 ggg cca cag cgc ttc tca gga gct cca gct atg atg gaa ggc tca tgg     607
Gly Pro Gln Arg Phe Ser Gly Ala Pro Ala Met Met Glu Gly Ser Trp
135                 140                 145                 150 ttg gat gtg gcc cag cga ggc aag cct gag gcc cag cca ttt gca cac     655
Leu Asp Val Ala Gln Arg Gly Lys Pro Glu Ala Gln Pro Phe Ala His
                155                 160                 165 ctc acc atc aat gct gcc agc atc cca tcg ggt tcc cat aaa gtc act     703
Leu Thr Ile Asn Ala Ala Ser Ile Pro Ser Gly Ser His Lys Val Thr
            170                 175                 180 ctg tcc tct tgg tac cac gat cga ggc tgg gcc aag atc tct aac atg     751
Leu Ser Ser Trp Tyr His Asp Arg Gly Trp Ala Lys Ile Ser Asn Met
        185                 190                 195 acg tta agc aac gga aaa cta agg gtt aac caa gat ggc ttc tat tac     799
Thr Leu Ser Asn Gly Lys Leu Arg Val Asn Gln Asp Gly Phe Tyr Tyr
    200                 205                 210 ctg tac gcc aac att tgc ttt cgg cat cat gaa aca tcg gga agc gta     847
Leu Tyr Ala Asn Ile Cys Phe Arg His His Glu Thr Ser Gly Ser Val
215                 220                 225                 230 cct aca gac tat ctt cag ctg atg gtg tat gtc gtt aaa acc agc atc     895
Pro Thr Asp Tyr Leu Gln Leu Met Val Tyr Val Val Lys Thr Ser Ile
                235                 240                 245 aaa atc cca agt tct cat aac ctg atg aaa gga ggg agc acg aaa aac     943
Lys Ile Pro Ser Ser His Asn Leu Met Lys Gly Gly Ser Thr Lys Asn
            250                 255                 260 tgg tcg ggc aat tct gaa ttc cac ttt tat tcc ata aat gtt ggg gga     991
Trp Ser Gly Asn Ser Glu Phe His Phe Tyr Ser Ile Asn Val Gly Gly
```

-continued

```
                265                 270                 275
ttt ttc aag ctc cga gct ggt gaa gaa att agc att cag gtg tcc aac     1039
Phe Phe Lys Leu Arg Ala Gly Glu Glu Ile Ser Ile Gln Val Ser Asn
    280                 285                 290 cct tcc ctg ctg gat ccg gat caa gat gcg acg tac ttt ggg gct ttc     1087
Pro Ser Leu Leu Asp Pro Asp Gln Asp Ala Thr Tyr Phe Gly Ala Phe
295                 300                 305                 310 aaa gtt cag gac ata gac tgagactcat tcgtggaac attagcatgg              1135
Lys Val Gln Asp Ile Asp
                315 atgtcctaga tgtttggaaa cttcttaaaa aatggatgat gtctatacat gtgtaagact    1195 actaagagac atggcccacg gtgtatgaaa ctcacagccc tctctcttga gcctgtacag    1255 gttgtgtata tgtaaagtcc ataggtgatg ttagattcat ggtgattaca caacggtttt    1315 acaattttgt aatgatttcc tagaattgaa ccagattggg agaggtattc cgatgcttat    1375 gaaaaactta cacgtgagct atggaagggg gtcacagtct ctgggtctaa cccctggaca    1435 tgtgccactg agaaccttga aattaagagg atgccatgtc attgcaaaga atgatagtg     1495 tgaagggtta agttcttttg aattgttaca ttgcgctggg acctgcaaat aagttctttt    1555 tttctaatga ggagagaaaa atatatgtat ttttatataa tgtctaaagt tatatttcag    1615 gtgtaatgtt ttctgtgcaa agttttgtaa attatatttg tgctatagta tttgattcaa    1675 aatatttaaa aatgtctcac tgttgacata tttaatgttt taaatgtaca gatgtattta    1735 actggtgcac tttgtaattc ccctgaaggt actcgtagct aagggggcag aatactgttt    1795 ctggtgacca catgtagttt atttctttat tcttttttaac ttaatagagt cttcagactt   1855 gtcaaaacta tgcaagcaaa ataaataaat aaaaataaaa tgaataccttt gaataataag   1915 taggatgttg gtcaccaggt gcctttcaaa tttagaagct aattgacttt aggagctgac    1975 atagccaaaa aggatacata ataggctact gaaatctgtc aggagtattt atgcaattat    2035 tgaacaggtg tctttttttta caagagctac aaattgtaaa ttttgtttct tttttttccc   2095 atagaaaatg tactatagtt tatcagccaa aaaacaatcc acttttaat ttagtgaaag     2155 ttattttatt atactgtaca ataaaagcat tgtctctgaa tgttaatttt ttggtacaaa    2215 aaataaattt gtacgaaaac ctgaaaaaaa aaaaaaaaa aaaaaaagg gcggccgctc      2275 tagagggccc tattctatag                                                2295
```

<210> SEQ ID NO 2
<211> LENGTH: 316
<212> TYPE: PRT
<213> ORGANISM: Mouse

<400> SEQUENCE: 2

```
Met Arg Arg Ala Ser Arg Asp Tyr Gly Lys Tyr Leu Arg Ser Glu
 1               5                  10                  15

Glu Met Gly Ser Gly Pro Gly Val Pro His Glu Gly Pro Leu His Pro
             20                  25                  30

Ala Pro Ser Ala Pro Ala Pro Pro Pro Ala Ala Ser Arg Ser
         35                  40                  45

Met Phe Leu Ala Leu Leu Gly Leu Gly Leu Gly Gln Val Val Cys Ser
     50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                 85                  90                  95
```

-continued

```
Asn Ala Gly Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
    130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
        195                 200                 205

Gln Asp Gly Phe Tyr Tyr Leu Tyr Ala Asn Ile Cys Phe Arg His His
    210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
        275                 280                 285

Ser Ile Gln Val Ser Asn Pro Ser Leu Leu Asp Pro Asp Gln Asp Ala
    290                 295                 300

Thr Tyr Phe Gly Ala Phe Lys Val Gln Asp Ile Asp
305                 310                 315

<210> SEQ ID NO 3
<211> LENGTH: 2271
<212> TYPE: DNA
<213> ORGANISM: Human
<220> FEATURE:
<221> NAME/KEY: CDS
<222> LOCATION: (185)..(1135)

<400> SEQUENCE: 3
aagcttggta ccgagctcgg atccactact cgacccacgc gtccgcgcgc cccaggagcc      60
aaagccgggc tccaagtcgg cgccccacgt cgaggctccg ccgcagcctc cggagttggc     120
cgcagacaag aaggggaggg agcgggagag ggaggagagc tccgaagcga gagggccgag     180 cgcc atg cgc cgc gcc agc aga gac tac acc aag tac ctg cgt ggc tcg     229
     Met Arg Arg Ala Ser Arg Asp Tyr Thr Lys Tyr Leu Arg Gly Ser
     1               5                  10                  15 gag gag atg ggc ggc ggc ccc gga gcc ccg cac gag ggc ccc ctg cac     277
Glu Glu Met Gly Gly Gly Pro Gly Ala Pro His Glu Gly Pro Leu His
            20                  25                  30 gcc ccg ccg ccg cct gcg ccg cac cag ccc ccc gcc gcc tcc cgc tcc     325
Ala Pro Pro Pro Pro Ala Pro His Gln Pro Pro Ala Ala Ser Arg Ser
        35                  40                  45 atg ttc gtg gcc ctc ctg ggg ctg ggg ctg ggc cag gtt gtc tgc agc     373
Met Phe Val Ala Leu Leu Gly Leu Gly Leu Gly Gln Val Val Cys Ser
    50                  55                  60 gtc gcc ctg ttc ttc tat ttc aga gcg cag atg gat cct aat aga ata     421
Val Ala Leu Phe Phe Tyr Phe Arg Ala Gln Met Asp Pro Asn Arg Ile
65                  70                  75
```

| | | |
|---|---|---|
| tca gaa gat ggc act cac tgc att tat aga att ttg aga ctc cat gaa<br>Ser Glu Asp Gly Thr His Cys Ile Tyr Arg Ile Leu Arg Leu His Glu<br>80                          85                     90                    95 | 469 |
| aat gca gat ttt caa gac aca act ctg gag agt caa gat aca aaa tta<br>Asn Ala Asp Phe Gln Asp Thr Thr Leu Glu Ser Gln Asp Thr Lys Leu<br>                  100                     105                     110 | 517 |
| ata cct gat tca tgt agg aga att aaa cag gcc ttt caa gga gct gtg<br>Ile Pro Asp Ser Cys Arg Arg Ile Lys Gln Ala Phe Gln Gly Ala Val<br>               115                     120                     125 | 565 |
| caa aag gaa tta caa cat atc gtt gga tca cag cac atc aga gca gag<br>Gln Lys Glu Leu Gln His Ile Val Gly Ser Gln His Ile Arg Ala Glu<br>        130                     135                     140 | 613 |
| aaa gcg atg gtg gat ggc tca tgg tta gat ctg gcc aag agg agc aag<br>Lys Ala Met Val Asp Gly Ser Trp Leu Asp Leu Ala Lys Arg Ser Lys<br>145                         150                     155 | 661 |
| ctt gaa gct cag cct ttt gct cat ctc act att aat gcc acc gac atc<br>Leu Glu Ala Gln Pro Phe Ala His Leu Thr Ile Asn Ala Thr Asp Ile<br>160                         165                     170                    175 | 709 |
| cca tct ggt tcc cat aaa gtg agt ctg tcc tct tgg tac cat gat cgg<br>Pro Ser Gly Ser His Lys Val Ser Leu Ser Ser Trp Tyr His Asp Arg<br>                  180                     185                     190 | 757 |
| ggt tgg gcc aag atc tcc aac atg act ttt agc aat gga aaa cta ata<br>Gly Trp Ala Lys Ile Ser Asn Met Thr Phe Ser Asn Gly Lys Leu Ile<br>               195                     200                     205 | 805 |
| gtt aat cag gat ggc ttt tat tac ctg tat gcc aac att tgc ttt cga<br>Val Asn Gln Asp Gly Phe Tyr Tyr Leu Tyr Ala Asn Ile Cys Phe Arg<br>        210                     215                     220 | 853 |
| cat cat gaa act tca gga gac cta gct aca gag tat ctt caa cta atg<br>His His Glu Thr Ser Gly Asp Leu Ala Thr Glu Tyr Leu Gln Leu Met<br>225                         230                     235 | 901 |
| gtg tac gtc act aaa acc agc atc aaa atc cca agt tct cat acc ctg<br>Val Tyr Val Thr Lys Thr Ser Ile Lys Ile Pro Ser Ser His Thr Leu<br>240                         245                     250                    255 | 949 |
| atg aaa gga gga agc acc aag tat tgg tca ggg aat tct gaa ttc cat<br>Met Lys Gly Gly Ser Thr Lys Tyr Trp Ser Gly Asn Ser Glu Phe His<br>                  260                     265                     270 | 997 |
| ttt tat tcc ata aac gtt ggt gga ttt ttt aag tta cgg tct gga gag<br>Phe Tyr Ser Ile Asn Val Gly Gly Phe Phe Lys Leu Arg Ser Gly Glu<br>               275                     280                     285 | 1045 |
| gaa atc agc atc gag gtc tcc aac ccc tcc tta ctg gat ccg gat cag<br>Glu Ile Ser Ile Glu Val Ser Asn Pro Ser Leu Leu Asp Pro Asp Gln<br>        290                     295                     300 | 1093 |
| gat gca aca tac ttt ggg gct ttt aaa gtt cga gat ata gat<br>Asp Ala Thr Tyr Phe Gly Ala Phe Lys Val Arg Asp Ile Asp<br>305                         310                     315 | 1135 |
| tgagccccag tttttggagt gttatgtatt tcctggatgt ttggaaacat tttttaaaac | 1195 |
| aagccaagaa agatgtatat aggtgtgtga gactactaag aggcatggcc ccaacggtac | 1255 |
| acgactcagt atccatgctc ttgaccttgt agagaacacg cgtatttaca gccagtggga | 1315 |
| gatgttagac tcatggtgtg ttacacaatg gtttttaaat tttgtaatga attcctagaa | 1375 |
| ttaaaccaga ttggagcaat tacgggttga ccttatgaga aactgcatgt gggctatggg | 1435 |
| aggggttggt ccctggtcat gtgccccttc gcagctgaag tggagagggt gtcatctagc | 1495 |
| gcaattgaag gatcatctga aggggcaaat tcttttgaat tgttacatca tgctggaacc | 1555 |
| tgcaaaaaat acttttctta atgaggagag aaaatatatg tatttttata taatatctaa | 1615 |
| agttatattt cagatgtaat gttttctttg caaagtattg taaattatat ttgtgctata | 1675 |

```
gtatttgatt caaatatttt aaaaatgtct tgctgttgac atatttaatg ttttaaatgt    1735
acagacatat ttaactggtg cactttgtaa attccctggg gaaaacttgc agctaaggag    1795
gggaaaaaaa tgttgtttcc taatatcaaa tgcagtatat tcttcgttc ttttaagtt     1855 aatagatttt ttcagacttg tcaagcctgt gcaaaaaaat taaaatggat gccttgaata    1915
ataagcagga tgttggccac caggtgcctt tcaaatttag aaactaattg acttagaaa    1975 gctgacattg ccaaaagga tacataatgg gccactgaaa tctgtcaaga gtagttatat    2035
aattgttgaa caggtgtttt tccacaagtg ccgcaaattg taccttttt ttttttcaa     2095 aatagaaaag ttattagtgg tttatcagca aaaagtcca attttaattt agtaaatgtt    2155
atcttatact gtacaataaa acattgcct ttgaatgtta atttttttggt acaaaaataa    2215 atttatatga aaaaaaaaa aaagggcgg ccgctctaga gggccctatt ctatag          2271
```

<210> SEQ ID NO 4
<211> LENGTH: 317
<212> TYPE: PRT
<213> ORGANISM: Human

<400> SEQUENCE: 4

```
Met Arg Arg Ala Ser Arg Asp Tyr Thr Lys Tyr Leu Arg Gly Ser Glu
 1               5                  10                  15

Glu Met Gly Gly Gly Pro Gly Ala Pro His Glu Gly Pro Leu His Ala
            20                  25                  30

Pro Pro Pro Ala Pro His Gln Pro Ala Ser Arg Ser Met
        35                  40                  45

Phe Val Ala Leu Leu Gly Leu Gly Leu Gly Gln Val Val Cys Ser Val
        50                  55                  60

Ala Leu Phe Phe Tyr Phe Arg Ala Gln Met Asp Pro Asn Arg Ile Ser
 65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270
```

```
Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
        290                 295                 300

Ala Thr Tyr Phe Gly Ala Phe Lys Val Arg Asp Ile Asp
305                 310                 315

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
gttctcctca tatggatcca aaccgtattt ctgaagacag cactcactgc tt           52

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
tacgcactcc gcggttagtc tatgtcctga actttga                            37

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
atttgattct agaaggagga ataacatatg catgaaaacg caggtctgca g            51

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
tatccgcgga tcctcgagtt agtctatgtc ctgaactttg aa                      42

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
atttgattct agaaggagga ataacatatg tctgaagaca ctctgccgga ctcc         54

<210> SEQ ID NO 10
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      Oligonucleotide

<400> SEQUENCE: 10
tatccgcgga tcctcgagtt agtctatgtc ctgaactttg aa                              42

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
atttgattct agaaggagga ataacatatg aaacaagctt ttcagggg                        48

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
tatccgcgga tcctcgagtt agtctatgtc ctgaactttg aa                              42

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
atttgattct agaaggagga ataacatatg aaagaactgc agcacattgt g                    51

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
tatccgcgga tcctcgagtt agtctatgtc ctgaactttg aa                              42

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15
atttgattct agaaggagga ataacatatg cagcgtttct ctggtgctcc a                    51

<210> SEQ ID NO 16
<211> LENGTH: 42
<212> TYPE: DNA
<213> ORGANISM: Artificial Sequence
<220> FEATURE:
```

<223> OTHER INFORMATION: Description of Artificial Sequence: Synthetic
      Oligonucleotide

<400> SEQUENCE: 16
tatccgcgga tcctcgagtt agtctatgtc ctgaactttg aa                              42

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
gttctcctca tatggaaggt tcttggttgg atgtggccca                                 40

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 18
tacgcactcc gcggttagtc tatgtcctga actttga                                    37

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19
gttctcctca tatgcgtggt aaacctgaag ctcaaccatt tgca                            44

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
tacgcactcc gcggttagtc tatgtcctga actttga                                    37

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
gttctcctca tatgaaacct gaagctcaac catttgcaca cctcaccatc aat                  53

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 22
tacgcactcc gcggttagtc tatgtcctga actttga          37

<210> SEQ ID NO 23
<211> LENGTH: 65
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23
gttctcctca tatgcattta actattaacg ctgcatctat cccatcgggt tcccataaag    60
tcact                                                                65

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 24
tacgcactcc gcggttagtc tatgtcctga actttga          37

<210> SEQ ID NO 25
<211> LENGTH: 59
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 25
gttctcctca tatgactatt aacgctgcat ctatcccatc gggttcccat aaagtcact    59

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 26
tacgcactcc gcggttagtc tatgtcctga actttga          37

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 27
cctctaggcc tgtactttcg agcgcagatg          30

<210> SEQ ID NO 28
<211> LENGTH: 32
<212> TYPE: DNA
<213> ORGANISM: Artificial Sequence
<220> FEATURE:

```
<223> OTHER INFORMATION: Description of Artificial Sequence: Synthetic
      Oligonucleotide

<400> SEQUENCE: 28
cctctgcggc cgcgtctatg tcctgaactt tg                                    32

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 29
cctctctcga gtggacaacc cagaagcctg aggcccagcc atttgc                     46

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 30
cctctgcggc cgcgtctatg tcctgaactt tg                                    32

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 31
agcttccacc atgaacaagt ggctgtgctg cgcactcctg gtgctcctgg acatca         56

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 32
tcgatgatgt ccaggagcac caggagtgcg cagcacagcc acttgttcat ggtgga         56

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Asn Ala Ala Ser Ile Pro Ser Gly Ser His Lys Val Thr Leu Ser Ser
  1               5                  10                  15
Trp Tyr His Asp Arg Gly Thr Ala Lys Ile Ser
             20                  25

<210> SEQ ID NO 34
<211> LENGTH: 28
```

<212> TYPE: PRT
<213> ORGANISM: Artificial Sequence
<220> FEATURE:
<223> OTHER INFORMATION: Description of Artificial Sequence: Synthetic
      Oligonucleotide

<400> SEQUENCE: 34

Asn Ala Ala Ser Ile Pro Ser Gly Ser His Lys Val Thr Leu Ser Ser
 1               5                  10                  15
Trp Tyr His Asp Arg Gly Trp Ala Lys Ile Ser Cys
            20                  25

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Val Tyr Val Val Lys Thr Ser Ile Lys Ile Pro Ser Ser His Asn Leu
 1               5                  10                  15
Met

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 36
tctccaagct tgtgactctc caggtcactc c                                  31

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      Peptide

<400> SEQUENCE: 37
tctccgcggc cgcgtaagcc tgggcctcat tgggtg                             36

<210> SEQ ID NO 38
<211> LENGTH: 72
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 38
ctagcaccat gaacaagtgg ctgtgctgcg cactcctggt gctcctggac atcattgaat   60
ggacaaccca ga                                                       72

<210> SEQ ID NO 39
<211> LENGTH: 72
<212> TYPE: DNA
<213> ORGANISM: Artificial Sequence
<220> FEATURE:
<223> OTHER INFORMATION: Description of Artificial Sequence: Synthetic
      Oligonucleotide

```
<400> SEQUENCE: 39
agcttctggg ttgtccattc aatgatgtcc aggagcacca ggagtgcgca gcacagccac    60
ttgttcatgg tg                                                        72

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      Oligonucleotide

<400> SEQUENCE: 40

Lys Leu Val Thr Leu Gln Val Thr Pro
  1               5
```